(12) United States Patent
Agian et al.

(10) Patent No.: US 12,138,157 B2
(45) Date of Patent: *Nov. 12, 2024

(54) ATRIOVENTRICULAR VALVE REPLACEMENT

(71) Applicant: Innovalve Bio Medical Ltd., Ramat-Gan (IL)

(72) Inventors: Nadav Agian, Kfar Yona (IL); Shai Karni, Rehovot (IL); Amit Tubishevitz, Tel Aviv (IL); Yuri Sudin, Modi'in-Makkabbimi-Re'ut (IL)

(73) Assignee: Innovalve Bio Medical Ltd., Ramat-Gan (IL)

(*) Notice: Subject to any disclaimer, the term of this patent is extended or adjusted under 35 U.S.C. 154(b) by 344 days.

This patent is subject to a terminal disclaimer.

(21) Appl. No.: 17/488,628

(22) Filed: Sep. 29, 2021

(65) Prior Publication Data

US 2022/0015900 A1    Jan. 20, 2022

Related U.S. Application Data

(63) Continuation of application No. 17/263,776, filed as application No. PCT/IB2020/057636 on Aug. 13, 2020, now Pat. No. 12,036,115.

(60) Provisional application No. 62/886,366, filed on Aug. 14, 2019.

(51) Int. Cl.
A61F 2/24 (2006.01)

(52) U.S. Cl.
CPC .......... *A61F 2/2418* (2013.01); *A61F 2/2409* (2013.01); *A61F 2/2427* (2013.01);
(Continued)

(58) Field of Classification Search
CPC .... A61F 2/2418; A61F 2/2436; A61F 2/2457; A61F 2/2466; A61F 2/2409;
(Continued)

(56) References Cited

U.S. PATENT DOCUMENTS

| | | |
|---|---|---|
| 6,270,520 B1 | 8/2001 | Inoue |
| 7,018,408 B2 | 3/2006 | Bailey et al. |

(Continued)

FOREIGN PATENT DOCUMENTS

| | | |
|---|---|---|
| CA | 2606101 A1 | 11/2006 |
| CA | 2898991 A1 | 8/2014 |

(Continued)

OTHER PUBLICATIONS

Communication Pursuant to Rule 94(3) for European Patent Application No. 20760551.0 mailed Apr. 7, 2022.

(Continued)

*Primary Examiner* — Katherine M Rodjom
(74) *Attorney, Agent, or Firm* — Dorsey & Whitney LLP

(57) ABSTRACT

Apparatus and methods are described including rotating at least a portion of a valve frame in a first direction and subsequently rotating the valve frame in a second direction. The valve frame includes chord-recruiting arms. An outer surface of each of the chord-recruiting arms has a smooth, convex curvature that extends along substantially a full length of the chord-recruiting arm, such that during the rotation of the portion of the valve frame in the first direction, the chords slide over the outer surface of the chord-recruiting arm without be recruited or caught by the chord-recruiting arm. An inner surface of each of the chord-recruiting arms has a concave curvature, such that during the rotation of the portion of the valve frame in the second direction, the chords are recruited within a space defined by the concave curvature.

25 Claims, 17 Drawing Sheets

(52) U.S. Cl.
CPC .......... *A61F 2/2436* (2013.01); *A61F 2/2457* (2013.01); *A61F 2/2466* (2013.01); *A61F 2220/0016* (2013.01); *A61F 2220/005* (2013.01); *A61F 2220/0058* (2013.01); *A61F 2220/0075* (2013.01); *A61F 2220/0091* (2013.01); *A61F 2230/0067* (2013.01); *A61F 2230/0069* (2013.01)

(58) Field of Classification Search
CPC ........ A61F 2220/0016; A61F 2220/005; A61F 2220/0058; A61F 2220/0075; A61F 2230/0067; A61F 2230/0069
See application file for complete search history.

(56) References Cited

U.S. PATENT DOCUMENTS

| | | |
|---|---|---|
| 7,621,948 B2 | 11/2009 | Herrmann et al. |
| 7,748,389 B2 | 7/2010 | Salahieh et al. |
| 7,753,949 B2 | 7/2010 | Lamphere et al. |
| 8,070,802 B2 | 12/2011 | Lamphere et al. |
| 8,870,950 B2 | 10/2014 | Hacohen |
| 9,364,326 B2 | 6/2016 | Yaron |
| 9,700,412 B2 | 7/2017 | Yaron et al. |
| 9,949,830 B2 | 4/2018 | Solem |
| 10,105,217 B2 | 10/2018 | Keränen |
| 10,130,471 B2 | 11/2018 | Keränen et al. |
| 10,238,489 B2 | 3/2019 | Conklin |
| 10,292,816 B2 | 5/2019 | Raanani et al. |
| 10,292,850 B2 | 5/2019 | Vad et al. |
| 10,500,038 B1 | 12/2019 | Orlov et al. |
| 11,065,114 B2 | 7/2021 | Raanani et al. |
| 11,583,394 B2 | 2/2023 | Orlov et al. |
| 11,779,459 B2 | 10/2023 | Raanani et al. |
| 2002/0065554 A1 | 5/2002 | Streeter |
| 2003/0014104 A1 | 1/2003 | Cribier |
| 2003/0083742 A1 | 5/2003 | Spence et al. |
| 2004/0138745 A1 | 7/2004 | Macoviak et al. |
| 2005/0165479 A1 | 7/2005 | Drews et al. |
| 2006/0195134 A1 | 8/2006 | Crittenden |
| 2006/0195184 A1 | 8/2006 | Lane et al. |
| 2006/0241745 A1 | 10/2006 | Solem |
| 2007/0016288 A1 | 1/2007 | Gurskis et al. |
| 2007/0050020 A1 | 3/2007 | Spence |
| 2007/0260305 A1 | 11/2007 | Drews et al. |
| 2008/0039935 A1 | 2/2008 | Buch et al. |
| 2009/0192585 A1 | 7/2009 | Bloom et al. |
| 2009/0192586 A1 | 7/2009 | Tabor et al. |
| 2009/0198324 A1 | 8/2009 | Orlov |
| 2010/0022640 A1 | 1/2010 | Stoutamire |
| 2010/0042208 A1 | 2/2010 | Herrmann et al. |
| 2010/0049313 A1 | 2/2010 | Alon et al. |
| 2010/0249923 A1 | 9/2010 | Alkhatib et al. |
| 2010/0331971 A1 | 12/2010 | Keraenen et al. |
| 2011/0029072 A1 | 2/2011 | Gabbay |
| 2011/0137397 A1 | 6/2011 | Chau et al. |
| 2011/0137410 A1 | 6/2011 | Hacohen |
| 2011/0224785 A1 | 9/2011 | Hacohen |
| 2011/0264208 A1 | 10/2011 | Duffy et al. |
| 2012/0010461 A1 | 1/2012 | Goldfarb et al. |
| 2012/0022639 A1 | 1/2012 | Hacohen et al. |
| 2012/0022640 A1 | 1/2012 | Gross et al. |
| 2012/0101571 A1 | 4/2012 | Thambar et al. |
| 2013/0035759 A1 | 2/2013 | Gross et al. |
| 2013/0166022 A1 | 6/2013 | Conklin |
| 2014/0031928 A1* | 1/2014 | Murphy ................ A61F 2/2418 623/2.37 |
| 2014/0088695 A1 | 3/2014 | Figulla et al. |
| 2014/0088696 A1 | 3/2014 | Figulla et al. |
| 2014/0222136 A1 | 8/2014 | Geist et al. |
| 2014/0379074 A1 | 12/2014 | Spence et al. |
| 2015/0045880 A1 | 2/2015 | Hacohen |
| 2015/0173897 A1* | 6/2015 | Raanani ................ A61F 2/2436 623/2.11 |
| 2015/0351903 A1 | 12/2015 | Morriss et al. |
| 2015/0351908 A1 | 12/2015 | Kernen et al. |
| 2015/0359628 A1 | 12/2015 | Keränen |
| 2015/0374493 A1 | 12/2015 | Yaron et al. |
| 2016/0045306 A1* | 2/2016 | Agrawal ............... A61F 2/2418 623/2.38 |
| 2016/0095705 A1 | 4/2016 | Keränen et al. |
| 2017/0128199 A1 | 5/2017 | Gurovich et al. |
| 2017/0281338 A1 | 10/2017 | Quill et al. |
| 2018/0014932 A1 | 1/2018 | Hammer et al. |
| 2018/0125651 A1* | 5/2018 | Nasr ..................... A61F 2/2418 |
| 2018/0177594 A1* | 6/2018 | Patel .................... A61F 2/243 |
| 2018/0206992 A1* | 7/2018 | Brown ............ A61B 17/12013 |
| 2019/0083245 A1* | 3/2019 | Hariton ................ A61F 2/2436 |
| 2019/0110893 A1* | 4/2019 | Haarer .................... A61F 2/246 |
| 2019/0125534 A1 | 5/2019 | Arcaro et al. |
| 2019/0231522 A1 | 8/2019 | Raanani et al. |
| 2020/0100898 A1 | 4/2020 | Vola et al. |
| 2020/0197175 A1 | 6/2020 | Chang et al. |
| 2022/0015896 A1 | 1/2022 | Agian et al. |
| 2022/0015905 A1 | 1/2022 | Raanani et al. |
| 2022/0296370 A1 | 9/2022 | Agian et al. |

FOREIGN PATENT DOCUMENTS

| | | |
|---|---|---|
| CN | 101180010 A | 5/2008 |
| CN | 102292053 A | 12/2011 |
| CN | 102438546 A | 5/2012 |
| CN | 104684505 A | 6/2015 |
| CN | 104994812 A | 10/2015 |
| DE | 102006052564 | 12/2007 |
| EP | 1850796 B1 | 12/2015 |
| EP | 3399947 A1 | 11/2018 |
| EP | 2948102 B1 | 1/2019 |
| EP | 2852354 B1 | 5/2020 |
| JP | 2008536592 A | 9/2008 |
| JP | 2011509806 A | 3/2011 |
| JP | 2012500665 A | 1/2012 |
| JP | 2012521222 A | 9/2012 |
| JP | 2014168694 A | 9/2014 |
| JP | 2015517376 A | 6/2015 |
| JP | 2016504134 A | 2/2016 |
| JP | 2018501001 A | 1/2018 |
| JP | 2019500965 A | 1/2019 |
| JP | 7051736 B2 | 4/2022 |
| WO | 0060995 A2 | 10/2000 |
| WO | 2004032724 A2 | 4/2004 |
| WO | 2005087140 A1 | 9/2005 |
| WO | 2006116558 A2 | 11/2006 |
| WO | 2007135101 A1 | 11/2007 |
| WO | 2009134701 A2 | 11/2009 |
| WO | 2010108079 A1 | 9/2010 |
| WO | 2012004679 A2 | 1/2012 |
| WO | 2012095116 A1 | 7/2012 |
| WO | 2013001339 A2 | 1/2013 |
| WO | 2013175468 A2 | 11/2013 |
| WO | 2014114795 A1 | 7/2014 |
| WO | 2015198125 A1 | 12/2015 |
| WO | 2018109329 A1 | 6/2018 |
| WO | 2018112429 A1 | 6/2018 |
| WO | 2020092096 A2 | 5/2020 |
| WO | 2020100050 A1 | 5/2020 |
| WO | 2021028867 A1 | 2/2021 |
| WO | 2022090881 A1 | 5/2022 |
| WO | 2022090882 A1 | 5/2022 |
| WO | 2022234468 A1 | 11/2022 |
| WO | 2022264082 A1 | 12/2022 |
| WO | 2023228028 A1 | 11/2023 |
| WO | 2024057226 A1 | 3/2024 |

OTHER PUBLICATIONS

International Search Report and Written Opinion for International Application No. PCT/IB2021/059798 mailed Jan. 24, 2022.
International Search Report and Written Opinion for International Application No. PCT/IB2021/059799 mailed Jan. 25, 2022.
Non-Final Office Action for U.S. Appl. No. 16/655,656 mailed Jun. 17, 2022.

(56) References Cited

OTHER PUBLICATIONS

Office Action for Japanese Application No. 2019/032726 mailed Nov. 19, 2021.
U.S. Appl. No. 17/263,776, filed Jan. 27, 2021.
U.S. Appl. No. 17/488,623, filed Sep. 29, 2021.
U.S. Appl. No. 62/767,018, filed Nov. 14, 2018.
Extended European Search Report for European Application No. 23162937.9 mailed Jun. 21, 2023.
Notice of Allowance for U.S. Appl. No. 17/349,152 mailed May 24, 2023.
Office Action for Canadian Application No. 3,149,527 mailed Mar. 6, 2023.
U.S. Appl. No. 16/106,000, filed Oct. 27, 2020.
U.S. Appl. No. 16/106,034, filed Oct. 27, 2020.
U.S. Appl. No. 18/248,394, filed Apr. 10, 2023.
U.S. Appl. No. 63/106,000, filed Oct. 27, 2020.
U.S. Appl. No. 63/106,034, filed Oct. 27, 2020.
Examination Report for Indian Application No. 202170217772 mailed Jan. 11, 2023.
Hearing Notice for Indian Application No. 2424/MUMNP/2014 mailed Jan. 3, 2023.
International Search Report and Written Opinion from International Application No. PCT/IB2022/055593 mailed Nov. 14, 2022.
Invitation to Pay Additional Fees for International Application No. PCT/IB2022/055593 mailed Sep. 23, 2022.
U.S. Appl. No. 17/349,152, filed Jun. 16, 2021.
U.S. Appl. No. 17/932,014, filed Sep. 14, 2022.
U.S. Appl. No. 63/211,602, filed Jun. 17, 2021.
International Search Report and Written Opinion from International Application No. PCT/IB2022/054099 mailed Sep. 12, 2022.
Invitation to Pay Additional Fees for International Application No. PCT/IB2022/054099 mailed Jul. 20, 2022.
U.S. Appl. No. 63/184,403, filed May 5, 2021.
U.S. Appl. No. 63/184,427, filed May 5, 2021.
Advisory Action for U.S. Appl. No. 14/402,387 mailed Mar. 1, 2018.
Communication Pursuant to Article 94(3) EPC Dated Jan. 8, 2018 From the European Patent Office Re. Application No. 13732633.6.
Communication Relating to the Results of the Partial International Search Dated Nov. 18, 2013 From the International Searching Authority Re. Application No. PCT/IL2013/050432.
Corrected Notice of Allowability for U.S. Appl. No. 14/402,387 mailed Mar. 20, 2019.
Examination Report for Australian Application No. 2013264730 mailed Dec. 20, 2017.
Examination Report for Australian Application No. 2013264730 mailed Jan. 13, 2017.
Examination Report for Australian Application No. 2018202951 mailed Dec. 6, 2018.
Examination Report for Australian Application No. 2019250140 mailed Oct. 19, 2020.
Examination Report for European Application No. 13732633.6 mailed Aug. 8, 2019.
Examination Report for Indian Application No. 2424/MUMNP/2014 mailed Aug. 31, 2020.
Final Office Action for U.S. Appl. No. 14/402,387 mailed Oct. 2, 2017.
Final Office Action for U.S. Appl. No. 13/475,994 mailed Jan. 10, 2017.
Final Office Action for U.S. Appl. No. 13/475,994 mailed Jun. 10, 2015.
International Preliminary Report on Patentability from International Application No. PCT/IL2013/050432 mailed Dec. 4, 2014.
International Search Report and Written Opinion from International Application No. PCT/IB2019/059734 mailed Feb. 6, 2020.
International Search Report and Written Opinion from International Application No. PCT/IB2020/057636 mailed Oct. 29, 2020.
International Search Report and Written Opinion from International Application No. PCT/IL2013/050432 mailed Feb. 26, 2014.
Issue Notification for U.S. Appl. No. 14/402,387 mailed May 1, 2019.
Issue Notification for U.S. Appl. No. 16/374,240 mailed Jun. 30, 2021.
Non-Final Office Action for U.S. Appl. No. 13/475,994 mailed Apr. 1, 2016.
Non-Final Office Action for U.S. Appl. No. 13/475,994 mailed Oct. 1, 2014.
Non-Final Office Action for U.S. Appl. No. 13/475,994 mailed Sep. 11, 2017.
Non-Final Office Action for U.S. Appl. No. 14/402,387 mailed Dec. 23, 2016.
Non-Final Office Action for U.S. Appl. No. 14/402,387 mailed Sep. 20, 2018.
Notice of Allowance for U.S. Appl. No. 14/402,387 mailed Apr. 30, 2019.
Notice of Allowance for U.S. Appl. No. 14/402,387 mailed Jan. 30, 2019.
Notice of Allowance for U.S. Appl. No. 16/374,240 mailed Mar. 16, 2021.
Notice of Amendment Dated Jun. 23, 2017 From the State Intellectual Property Office of the People's Republic of China Re. Application No. 201710425696.6 and Its Machine Translation Into English.
Notice of Reason for Rejection Dated Feb. 14, 2017 From the Japan Patent Office Re. Application No. 2015-513347 and Translation.
Notification of Office Action and Search Report Dated Sep. 7, 2016 From the State Intellectual Property Office of the People's Republic of China Re. Application No. 201380038199.0.
Notification of Office Action Dated Dec. 3, 2015 From the State Intellectual Property Office of the People's Republic of China Re. Application No. 201380038199.0.
Notification of Office Action Dated Dec. 14, 2016 From the State Intellectual Property Office of the People's Republic of China Re. Application No. 201380038199.0 and Its Translation Into English.
Office Action for Australian Application No. 2018202951 mailed Apr. 1, 2019.
Office Action for Canadian Application No. 2,874,208 mailed Aug. 2, 2019.
Office Action for Canadian Application No. 2,874,208 mailed Feb. 19, 2019.
Office Action for Chinese Application No. 20170425696.6 mailed May 19, 2020.
Office Action for Chinese Application No. 201710425696.6 mailed Nov. 4, 2019.
Office Action for Japanese Application No. 2017-184962 mailed Jul. 31, 2018.
Office Action for Japanese Application No. 2019/032726 mailed Feb. 18, 2020.
Office Action for Japanese Application No. 2019/032726 mailed Jan. 19, 2021.
Restriction Requirement for U.S. Appl. No. 13/475,994 mailed Mar. 11, 2014.
Translation Dated Dec. 28, 2015 of Notification of Office Action Dated Dec. 3, 2015 From the State Intellectual Property Office of the People's Republic of China Re. Application No. 201380038199.0.
Translation of Notification of Office Action and Search Report Dated Sep. 7, 2016 From the State Intellectual Property Office of the People's Republic of China Re. Application No. 201380038199.0.
U.S. Appl. No. 12/582,986, filed Oct. 21, 2009.
U.S. Appl. No. 14/402,387, filed Nov. 20, 2014.
U.S. Appl. No. 16/374,240, filed Apr. 3, 2019.
U.S. Appl. No. 61/649,319, filed May 20, 2012.
U.S. Appl. No. 62/886,366, filed Aug. 14, 2019.
Applicant-Initiated Interview Summary for U.S. Appl. No. 14/402,387 mailed Dec. 28, 2017.
Applicant-Initiated Interview Summary for U.S. Appl. No. 14/402,387 mailed May 25, 2017.
Final Office Action for U.S. Appl. No. 13/083,643 mailed Mar. 5, 2014.
Final Office Action for U.S. Appl. No. 13/475,994 mailed Jun. 8, 2018.

(56) References Cited

OTHER PUBLICATIONS

International Search Report and Written Opinion from International Application No. PCT/IB2023/055160 mailed Jul. 28, 2023.
Issue Notification for U.S. Appl. No. 13/475,994 mailed Nov. 20, 2019.
Issue Notification for U.S. Appl. No. 16/655,656 mailed Feb. 1, 2023.
Issue Notification for U.S. Appl. No. 17/349,152 mailed Sep. 20, 2023.
Non-Final Office Action for U.S. Appl. No. 13/475,994 mailed Dec. 28, 2018.
Non-Final Office Action for U.S. Appl. No. 17/263,776 mailed Oct. 25, 2023.
Non-Final Office Action for U.S. Appl. No. 17/488,623 mailed Oct. 26, 2023.
Notice of Allowance for U.S. Appl. No. 13/475,994 mailed Jul. 22, 2019.
Notice of Allowance for U.S. Appl. No. 16/655,656 mailed Oct. 25, 2022.
Office Action for Japanese Application No. 2021-525788 mailed Nov. 1, 2023.
U.S. Appl. No. 13/475,994, filed May 20, 2012.
U.S. Appl. No. 16/655,656, filed Oct. 17, 2019.
U.S. Appl. No. 18/103,671, filed Jan. 31, 2023.
U.S. Appl. No. 61/488,180, filed May 20, 2011.
Examination Report for European Application No. 21801644.2 mailed May 2, 2024.
Final Office Action for U.S. Appl. No. 17/488,623 mailed May 30, 2024.
International Search Report and Written Opinion from International Application No. PCT/IB2023/059084 mailed Feb. 12, 2024.
Invitation to Pay Additional Fees for International Application No. PCT/IB2023/059084 mailed Dec. 22, 2023.
Non-Final Office Action for U.S. Appl. No. 17/292,987 mailed May 21, 2024.
Non-Final Office Action for U.S. Appl. No. 18/103,671 mailed Apr. 2, 2024.
Notice of Allowance for U.S. Appl. No. 17/263,776 mailed Apr. 9, 2024.
Notice of Allowance for U.S. Appl. No. 17/932,014 mailed May 22, 2024.
Office Action for Chinese Patent Application No. 201980082413 mailed Jan. 31, 2024.
Office Action for Israel Patent Application No. 283093 mailed Feb. 18, 2024.
Office Action for Japanese Application No. 2022-508890 mailed Apr. 9, 2024.
Office Action for Japanese Patent Application No. 2021-525788 mailed Mar. 11, 2024.
Office Action for Israel Application No. 290306 mailed Jul. 7, 2024.
Final Office Action for U.S. Appl. No. 18/103,671 mailed Jul. 29, 2024.
Issue Notification for U.S. Appl. No. 17/932,014 mailed Sep. 4, 2024.
Non-Final Office Action for U.S. Appl. No. 17/488,623 mailed Jul. 31, 2024.

* cited by examiner

ATRIOVENTRICULAR VALVE REPLACEMENT

CROSS-REFERENCES TO RELATED APPLICATIONS

The present application is a continuation of U.S. spplication Ser. No. 17/263,776 to Again filed Jan. 27, 2021, which is a U.S. national phase application of PCT Application No. PCT/IL/2020/057636 to Agian (published as WO 21/028867), filed Aug. 13, 2020, which claims priority from U.S. Provisional Patent Application 62/886,366 to Agian, filed Aug. 14, 2019, entitled "Atrioventricular valve replacement," which is incorporated herein by reference.

FIELD OF EMBODIMENTS OF THE INVENTION

The present invention relates to medical apparatus and methods, and specifically to apparatus and methods for implanting a prosthetic valve at an atrioventricular valve.

BACKGROUND

The human heart is a muscular organ that pumps deoxygenated blood through the lungs to oxygenate the blood and pumps oxygenated blood to the rest of the body by contractions of four chambers.

After having circulated in the body, deoxygenated blood from the body enters the right atrium through the vena cava. In a healthy subject, the right atrium contracts, pumping the blood through the tricuspid valve into the right ventricle. The right ventricle contracts, pumping the blood through the pulmonary semi-lunar valve into the pulmonary artery which splits to two branches, one for each lung. The blood is oxygenated while passing through the lungs, and reenters the heart via the left atrium. The left atrium contracts, pumping the oxygenated blood through the mitral valve into the left ventricle. The left ventricle contracts, pumping the oxygenated blood through the aortic valve into the aorta to be distributed to the rest of the body. The tricuspid valve closes during right ventricle contraction, so that backflow of blood into the right atrium is prevented. Similarly, the mitral valve closes during left ventricle contraction, so that backflow of blood into the left atrium is prevented. The mitral valve and the tricuspid valve are known as atrioventricular valves, each of these valves controlling the flow of blood between an atrium and a ventricle.

In the mitral valve, the mitral annulus defines a mitral valve orifice. An anterior leaflet and a posterior leaflet extend from the mitral annulus. The leaflets are connected by chords to papillary muscles within the left ventricle.

During ventricular diastole, in a healthy subject, the left atrium contracts to pump blood into the left ventricle through the mitral valve orifice. The blood flows through the orifice, pushing the leaflets apart and into the left ventricle with little resistance. In a healthy subject, the leaflets of the aortic valve are kept closed by blood pressure in the aorta.

During ventricular systole, the left ventricle contracts to pump blood into the aorta through the aortic valve, the leaflets of which are pushed open by the blood flow. In a healthy subject, the mitral annulus contracts, pushing the leaflets inwards and reducing the area of the mitral valve orifice by about 20% to 30%. The leaflets coapt to accommodate the excess leaflet surface area, producing a coaptation surface that constitutes a seal. The pressure of blood in the left ventricle pushes against the ventricular surfaces of the leaflets, tightly pressing the leaflets together at the coaptation surface so that a tight, leak-proof seal is formed.

An effective seal of the mitral valve during ventricular systole depends on a sufficient degree of coaptation. Improper coaptation may be caused by any number of physical anomalies that allow leaflet prolapse (for example, elongated or ruptured chords, or weak papillary muscles) or prevent coaptation (for example, short chords, or small leaflets). There are also pathologies that lead to a mitral valve insufficiency, including collagen vascular disease, ischemic mitral regurgitation (resulting, for example, from myocardial infarction, chronic heart failure, or failed/unsuccessful surgical or catheter revascularization), myxomatous degeneration of the leaflets, and rheumatic heart disease. Mitral valve regurgitation leads to many complications including arrhythmia, atrial fibrillation, cardiac palpitations, chest pain, congestive heart failure, fainting, fatigue, low cardiac output, orthopnea, paroxysmal nocturnal dyspnea, pulmonary edema, shortness of breath, and sudden death.

The tricuspid valve includes three leaflets: the septal leaflet, the anterior leaflet, and the posterior leaflet. Each of the valve leaflets is attached to the tricuspid valve annulus, which defines the tricuspid valve orifice. The leaflets are connected to papillary muscles within the right ventricle, by chords. In a healthy subject the tricuspid valve controls the direction of blood flow from the right atrium to the right ventricular, in a similar manner to the control of the mitral valve over the direction of blood flow on the left side of the heart. During ventricular diastole, the tricuspid valve opens, such as to allow the flow of blood from the right atrium to the right ventricle, and during ventricular systole the leaflets of the tricuspid valve coapt, such as to prevent the backflow of blood from the right ventricle to the right atrium.

Tricuspid valve regurgitation occurs when the tricuspid valve fails to close properly. This can cause blood to flow back up into the right atrium when the right ventricle contracts. Tricuspid valve regurgitation is most commonly caused by right ventricle dilation, which leads to the tricuspid valve annulus dilating, resulting in the valve leaflets failing to coapt properly.

SUMMARY OF EMBODIMENTS

For some applications of the present invention, a valve frame is provided for use with a prosthetic valve that is configured to be deployed within a native atrio-ventricular valve (e.g., the mitral valve, or the tricuspid valve). The valve frame typically includes a valve frame body that includes a cylindrical part, as well as an atrial part. Typically, the cylindrical part is configured to support a prosthetic valve within the native atrio-ventricular valve. For example, leaflets of the prosthetic valve may be sutured to the cylindrical part, and/or may be otherwise coupled to the cylindrical part. Typically, the atrial part is configured to be deployed at least partially within the subject's atrium. Further typically, the cylindrical part is configured to be deployed at least partially within the subject's ventricle.

For some applications, the atrial part includes a disc-shaped portion (also referred to herein as a flange) and a frustoconical portion. Typically, the disc-shaped portion of the atrial part is configured to seal the valve frame with respect to tissue on the atrial side of the native atrio-ventricular annulus, and is further configured to prevent migration of the valve frame into the ventricle. The frustoconical portion typically extends from the disc-shaped portion of the atrial part to the outer surface of the cylindrical part. For some applications, the inclusion of the frustoconical portion between the disc-shaped portion and the cylindrical part (as opposed to directly coupling the disc-shaped portion to the cylindrical part) reduces a likelihood of regurgitation around the outside of the cylindrical part.

For some applications, a plurality of chord-recruiting arms (e.g., more than two and/or fewer than twelve arms) extend from a portion of the valve-frame body that is configured to be placed within the subject's ventricle. For example, four chord-recruiting arms or six chord-recruiting arms may extend from the valve-frame body. For some applications, a single chord-fecruiting arm extends from a portion of valve-frame body that is configured to be placed within the subject's ventricle. Typically, the chord-recruiting arms extend from the cylindrical part of valve-frame body. Further typically, the chord-recruiting arms extend from a ventricular end of the cylindrical part (i.e., the end of the valve frame body that is configured to be placed within the ventricle). Typically, the arms extend radially from the valve-frame body, in addition to extending axially from the ventricular end of the valve-frame body toward an atrial end of the valve-frame body (i.e., the end of the valve frame body that is configured to be placed within the atrium). Further typically, the arms curve around outside of the valve-frame body in a given circumferential direction of curvature.

It is noted that descriptions herein of the arms extending from the valve-frame body in a given direction should not be interpreted as excluding additional directions in which the arms are oriented. Rather, the arms being described (or claimed) as extending radially from the valve-frame body should be interpreted as meaning that the orientation of the arms with respect to the valve-frame body includes a radial component. It is typically the case that, in addition to extending radially from the valve-frame body, the arms curve circumferentially, and in some cases the orientation of the arms includes an axial component. For some applications, at least along a portion of the arms, and at least in certain configurations of the arms, the arms are disposed tangentially with respect to the valve-frame body.

Typically, the valve frame, with prosthetic valve leaflets disposed therein, is delivered to the native atrio-ventricular valve, via a delivery device (e.g., a delivery catheter), and the delivery device is configured to maintain the valve frame and the prosthetic valve in radially-constrained configurations (i.e., "crimped" configurations) during the delivery. In accordance with respective applications, the valve frame is delivered transapically (i.e., via the apex of the left ventricle), transseptally (i.e., via the vena cava, the right atrium, and the interatrial septum), and/or via a different delivery path. For some applications, when a distal end of the delivery device is disposed within the subject's ventricle, the chord-recruiting arms are deployed among chords of the native atrio-ventricular valve.

Typically, the chord-recruiting arms are deployed among chords of the native atrio-ventricular valve by releasing the chord-recruiting arms from the delivery device, the chord-recruiting arms being shape set to extend from the valve-frame body, upon being released from the delivery device. For some applications, additional techniques are used in order to cause the chord-recruiting arms to become deployed among chords of the native atrio-ventricular valve by releasing the chord-recruiting arms from the delivery device. For example, the valve frame may include lever elements, which are configured to cause the chord-recruiting arms to extend radially. Alternatively or additionally, the arms are coupled to the cylindrical part of the valve frame via stitches, the stitches acting as hinges, such that the arms pivot about the stitches with respect to the cylindrical part, as described hereinbelow. Typically, the chord-recruiting arms are released from the delivery device while the valve-frame body is still maintained in an at least partially radially-constrained configuration by the delivery device. Further typically, in this configuration of the valve-frame body (i.e., with the chord-recruiting arms having been released from the delivery device, but with the valve-frame body still maintained in an at least partially radially-constrained configuration by the delivery device), the chord-recruiting arms assume a configuration that is described herein as the "rotation configuration" of the chord-recruiting arms.

Subsequent to the chord-recruiting arms being deployed among chords of the native atrio-ventricular valve (and typically while the valve-frame body is still maintained in the at least partially radially-constrained configuration by the delivery device), at least a portion of the valve frame is rotated, such as to cause the chord-recruiting arms to (a) pull the native atrio-ventricular valve radially inward toward the valve frame, and (b) twist the native atrio-ventricular valve around the valve frame, by recruiting and deflecting at least a portion of the chords.

Typically, the chord-recruiting arms are configured to curve in a given circumferential direction with respect to the longitudinal axis of the valve frame, both when the arms are deployed among the chords (i.e., when the arms are disposed in their rotation configuration), and when the valve-frame body is allowed to radially expand (i.e., when the valve frame assumes its non-radially constrained configuration), as described in further detail hereinbelow. For example, the arms may curve in a clockwise direction or in a counterclockwise direction with respect to the longitudinal axis of the valve frame. Typically, subsequent to the chord-recruiting arms being deployed among chords of the native atrio-ventricular valve (and typically while the valve-frame body is still maintained in the at least partially radially-constrained configuration by the delivery device), the valve frame is rotated in the same circumferential direction as the direction of the circumferential curvature of the arms. For some applications, prior to rotating the valve frame in this direction, the valve frame is rotated in the opposite circumferential direction. For example, if the arms curve in the clockwise circumferential direction, then, subsequent to the arms being deployed among the chords, the valve frame may first be rotated in the counterclockwise direction and may subsequently be rotated in the clockwise direction. For some applications, rotating the valve frame in this manner facilitates recruitment of a greater portion of the chords than if the valve frame were to only be rotated in the direction of the circumferential curvature of the arms.

As described in the above paragraph, for some applications, prior to rotating the valve frame in the same circumferential direction as the direction of the circumferential curvature of the arms, the valve frame is rotated in the opposite circumferential direction. For some applications, the delivery device is configured such as to perform the initial rotation of the valve frame through a given angle in the opposite circumferential direction from the direction of the circumferential curvature of the arms, and to subsequently rotate the valve frame though a predetermined angle in the direction of the circumferential curvature of the arms. For some applications, in the rotation configuration of the chord-recruiting arms, the outer surfaces of each of the arms has a smooth, convex curvature that extends along substantially the full length of the arm, such that during the initial rotation (against the direction of circumferential curvature of the arm) the chords slide over the outer surfaces of the arm without be recruited or caught by the arm, and without being damaged by the arms in any way. For some applications, by virtue of the arms being shaped in this manner, the initial rotation of the valve frame causes a relatively large number of chords to be positioned such as to be recruited by each of the arms in the subsequent rotation step. During the subsequent rotation of the valve frame (in the direction of the circumferential curvature of the arms), the chords are recruited and deflected (e.g., deflected inwardly) by the arms. Typically, in the rotation configuration of the chord-recruiting arms, the inner surface of the arm has a concave curvature and the chords are recruited within the space defined by the concave curvature, during the subsequent rotation by the valve frame.

For some applications, a plurality of struts protrude from the outside of the cylindrical part of the valve frame. Typically, the atrial part is coupled to the cylindrical part by the atrial part being coupled to the protruding struts, e.g., via stitching or welding. It is noted that, typically, during the crimping of the valve frame, there is a lot of strain that is placed on the junctions from which the protruding struts protrude from the cylindrical part, since the struts pivot about these junctions. If the atrial part were to be directly coupled to the cylindrical part at these junctions, then this would mean that these points at which there is relatively large strain placed on the valve frame are also points at which the two pieces are coupled to each other, which would make the frame susceptible to fatigue at these points. By contrast, by virtue of the cylindrical part including protruding struts and the atrial part being coupled to the cylindrical part via the struts, there is a separation between the points of high strain and the points at which atrial part is coupled to the cylindrical part.

It is further noted that, typically, the protruding struts protrude from an axial location along the cylindrical part that is in the lowest 90 percent (e.g., the lowest 70 percent, or the lowest 50 percent) of the height of the cylindrical part. Typically, the cylindrical part has a height of at least 15 mm, in order to accommodate the coupling of the valve leaflets to the cylindrical part. If the protruding struts were to protrude from the top of the cylindrical part (or if the atrial part were to be coupled directly to the cylindrical part at the top of the cylindrical part), then the entire height of the cylindrical part would be disposed below the atrial part. By contrast, since the protruding struts protrude from the lowest 90 percent (e.g., the lowest 70 percent, or the lowest 50 percent) of the height of the cylindrical part, there is typically axial overlap between the atrial part and the cylindrical part of the valve frame, along the height of the cylindrical part. Typically, this results in a smaller portion of the height of the cylindrical part protruding into the subject's ventricle, then if there were to be no axial overlap between the atrial part and the cylindrical part of the valve frame. In turn (when the valve frame is configured for placement within the subject's left ventricle), this typically reduces obstruction of the left ventricular outflow tract, relative to if a larger portion of the height of the cylindrical part were to protrude into the subject's ventricle. In this context, it is noted that, as described hereinabove, chord-recruiting arms are typically configured to (a) pull the native atrio-ventricular valve radially inward toward the valve frame, and (b) twist the native atrio-ventricular valve around the valve frame, by recruiting and deflecting at least a portion of the chords of the native atrioventricular valve. Typically, the recruitment and deflection of the chords in this manner serves to prevent obstruction of the left ventricular outflow tract by portions of the native mitral valve apparatus.

There is therefore provided, in accordance with some applications of the present invention, apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus including:

a valve frame configured to support the prosthetic valve within the native atrio-ventricular valve, the valve frame including:

an atrial part including a disc-shaped portion configured to be deployed on an atrial side of the valve annulus;

a cylindrical part to which the prosthetic valve leaflets are coupled, the cylindrical part configured to be deployed such that a ventricular end of the cylindrical part is disposed within the ventricle;

a plurality of chord-recruiting arms configured to extend at least radially from the ventricular end of the cylindrical part, the chord-recruiting arms being coupled to the ventricular end of the cylindrical part via stitches, and the stitches being configured to act as hinges, such that upon the chord-recruiting arms being released from a radially-constrained configuration, while the cylindrical part is held in an at least partially radially-constrained configuration, the chord-recruiting arms are configured to extend radially outwardly by pivoting about the stitches with respect to the cylindrical part.

In some applications, the atrial part further includes a frustoconical portion, and the frustoconical portion of the atrial part is coupled to the cylindrical part, such that there is axial overlap between at least the frustoconical portion of the atrial part and the cylindrical part.

In some applications, the atrial part further includes a frustoconical portion, the valve frame further includes a plurality of protruding struts that are configured to protrude from outside the cylindrical part, and the frustoconical portion of the atrial part is coupled to the cylindrical part via the protruding struts.

In some applications, the apparatus further includes a delivery device configured to:

deliver the valve frame to the native atrio-ventricular valve, subsequently, deploy the plurality of chord-recruiting arms among the chords of the native atrio-ventricular valve, and subsequently, rotate at least a portion of the valve frame, such as to cause the plurality of chord-recruiting arms to (a) pull the native atrio-ventricular valve radially inward toward the valve frame, and (b) twist the native atrio-ventricular valve around the valve frame, by recruiting and deflecting at least a portion of the chords.

In some applications:

the delivery device is configured to deploy the plurality of chord-recruiting arms among the chords of the native atrio-ventricular valve while maintaining the cylindrical part in at least partially radially constrained configuration, such that the chord-recruiting arms assume a rotation configuration in which the chord-recruiting arms extend at least radially from the ventricular end of the cylindrical part, and curve circumferentially around the cylindrical part in a given circumferential direction, and the delivery device is configured to rotate at least the portion of the valve frame, while the chord-recruiting arms are disposed in the rotation configuration.

In some applications, subsequent to rotating at least the portion of the valve frame, the delivery device is configured to release the atrial part and the cylindrical part of the valve frame, to thereby cause the native atrio-ventricular valve to be held (a) radially inwardly toward the valve frame, and (b) twisted around the valve frame, by causing at least a portion of the native atrio-ventricular valve to become trapped within the valve frame.

In some applications, when the atrial part and the cylindrical part of the valve frame have been released by the delivery device, the chord-recruiting arms are configured to define pockets, and the pockets defined by the chord-recruiting arms are configured to accommodate the trapped portion of the native atrio-ventricular valve.

In some applications:

the delivery device is configured, initially, to rotate at least the portion of the valve frame in an opposite circumferential direction from the direction of circumferential curvature of the chord-recruiting arms; and the delivery device is configured, subsequently, to rotate at least the portion of the valve frame in the direction of circumferential curvature of the chord-recruiting arms, such as to cause the plurality of chord-recruiting arms to (a) pull the native atrio-ventricular valve radially inward toward the valve frame, and (b) twist the native atrio-ventricular valve around the valve frame, by recruiting and deflecting at least the portion of the chords.

In some applications, in the rotation configuration of the chord-recruiting arms:

an outer surface of each of the chord-recruiting arms has a smooth, convex curvature that extends along substantially a full length of the chord-recruiting arm, such that during the rotation of at least the portion of the valve frame in the opposite circumferential direction from the direction of circumferential curvature of the chord-recruiting arms, chords slide over the outer surface of the chord-recruiting arm without be recruited or caught by the chord-recruiting arm; and an inner surface of each of the chord-recruiting arms has a concave curvature, such that during the rotation of at least the portion of the valve frame in the direction of circumferential curvature of the chord-recruiting arms, the chords are recruited within a space defined by the concave curvature.

In some applications, the disc-shaped portion of the atrial part includes struts that define cells, and at least some of the struts have an undulating pattern that are configured to provide the cells of the flange with flexibility, such that the disc-shaped portion is able to adapt its shape to conform with changes in a shape of tissue on the atrial side of the valve annulus.

In some applications, the cells of the disc-shaped portion are curved circumferentially, such that outer tips of the cells point in a given circumferential direction.

In some applications, the chord-recruiting arms are configured to curve around the cylindrical part circumferentially in an opposite direction of circumferential curvature from the given circumferential direction.

There is further provided, in accordance with some applications of the present invention, apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus including:

a valve frame configured to support the prosthetic valve within the native atrio-ventricular valve, the valve frame including:

an atrial part including a disc-shaped portion configured to be deployed on an atrial side of the valve annulus, and a frustoconical portion;

a cylindrical part to which the prosthetic valve leaflets are coupled, the cylindrical part configured to be deployed such that a ventricular end of the cylindrical part is disposed within the ventricle; and a plurality of protruding struts that are configured to protrude from outside the cylindrical part, the frustoconical portion of the atrial part being coupled to the cylindrical part via the protruding struts.

In some applications, the frustoconical portion of the atrial part is coupled to the cylindrical part, such that there is axial overlap between at least the frustoconical portion of the atrial part and the cylindrical part.

In some applications, the plurality of protruding struts protrude from outside the cylindrical part from an axial location along the cylindrical part that is in a lowest 70 percent of a height of the cylindrical part.

In some applications, the frustoconical portion of the atrial part is stitched to the protruding struts. In some applications, the frustoconical portion of the atrial part is welded to the protruding struts. In some applications, the frustoconical portion of the atrial part is glued to the protruding struts.

In some applications, by virtue of the frustoconical portion of the atrial part being coupled to the cylindrical part via the protruding struts, strain that is generated upon a region of the valve frame at which the frustoconical portion of the atrial part is coupled to the cylindrical part is reduced, relative to if the frustoconical portion of the atrial part were to be directly coupled to the cylindrical part.

In some applications, the valve frame further includes a plurality of chord-recruiting arms configured to extend at least radially from the ventricular end of the cylindrical part.

In some applications, the apparatus further includes a delivery device configured to:

deliver the valve frame to the native atrio-ventricular valve, subsequently, deploy the plurality of chord-recruiting arms among the chords of the native atrio-ventricular valve, and subsequently, rotate at least a portion of the valve frame, such as to cause the plurality of chord-recruiting arms to (a) pull the native atrio-ventricular valve radially inward toward the valve frame, and (b) twist the native atrio-ventricular valve around the valve frame, by recruiting and deflecting at least a portion of the chords.

In some applications, a tip of each of the chord-recruiting arms is rounded such as to guide chords around the tip of the chord-recruiting arm without damaging tissue.

In some applications, a tip of each of the chord-recruiting arms is cushioned such as to guide chords around the tip of the chord-recruiting arm without damaging tissue.

In some applications:

the delivery device is configured to deploy the plurality of chord-recruiting arms among the chords of the native atrio-ventricular valve, while maintaining the cylindrical part in at least partially radially constrained configuration, such that the chord-recruiting arms assume a rotation configuration in which the chord-recruiting arms extend at least radially from the ventricular end of the cylindrical part, and curve circumferentially around the cylindrical part in a given circumferential direction, and the delivery device is configured to rotate at least the portion of the valve frame, while the chord-recruiting arms are disposed in the rotation configuration.

In some applications, subsequent to rotating at least the portion of the valve frame, the delivery device is configured to release the atrial part and the cylindrical part of the valve frame, to thereby cause the native atrio-ventricular valve to be held (a) radially inwardly toward the valve frame, and (b) twisted around the valve frame, by causing at least a portion of the native atrio-ventricular valve to become trapped within the valve frame.

In some applications, when the atrial part and the cylindrical part of the valve frame have been released by the delivery device, the chord-recruiting arms are configured to define pockets, and the pockets defined by the chord-recruiting arms are configured to accommodate the trapped portion of the native atrio-ventricular valve.

In some applications:

the delivery device is configured, initially, to rotate at least the portion of the valve frame in an opposite circumferential direction from the direction of circumferential curvature of the chord-recruiting arms; and the delivery device is configured, subsequently, to rotate at least the portion of the valve frame in the direction of circumferential curvature of the chord-recruiting arms, such as to cause the plurality of chord-recruiting arms to (a) pull the native atrio-ventricular valve radially inward toward the valve frame, and (b) twist the native atrio-ventricular valve around the valve frame, by recruiting and deflecting at least the portion of the chords.

In some applications, in the rotation configuration of the chord-recruiting arms:

an outer surface of each of the chord-recruiting arms has a smooth, convex curvature that extends along substantially a full length of the chord-recruiting arm, such that during the rotation of at least the portion of the valve frame in the opposite circumferential direction from the direction of circumferential curvature of the chord-recruiting arms, chords slide over the outer surface of the chord-recruiting arm without be recruited or caught by the chord-recruiting arm; and an inner surface of each of the chord-recruiting arms has a concave curvature, such that during the rotation of at least the portion of the valve frame in the direction of circumferential curvature of the chord-recruiting arms, the chords are recruited within a space defined by the concave curvature.

In some applications, the disc-shaped portion of the atrial part includes struts that define cells, and at least some of the struts have an undulating pattern that are configured to provide the cells of the flange with flexibility, such that the disc-shaped portion is able to adapt its shape to conform with changes in a shape of tissue on the atrial side of the valve annulus.

In some applications, the cells of the disc-shaped portion are curved circumferentially, such that outer tips of the cells point in a given circumferential direction.

In some applications, the valve frame further includes chord-recruiting arms that are configured to curve around the cylindrical part circumferentially in an opposite direction of circumferential curvature from the given circumferential direction.

There is further provided, in accordance with some applications of the present invention, apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus including:

a valve frame configured to support the prosthetic valve within the native atrio-ventricular valve, the valve frame including:

an atrial part including a disc-shaped portion configured to be deployed on an atrial side of the valve annulus, and a frustoconical portion;

a cylindrical part to which the prosthetic valve leaflets are coupled, the cylindrical part configured to be deployed such that a ventricular end of the cylindrical part is disposed within the ventricle, the frustoconical portion of the atrial part being coupled to the cylindrical part, such that there is axial overlap between at least the frustoconical portion of the atrial part and the cylindrical part.

In some applications, the valve frame further includes a plurality of protruding struts that are configured to protrude from outside the cylindrical part, the frustoconical portion of the atrial part being coupled to the cylindrical part via the protruding struts.

In some applications, the frustoconical portion of the atrial part is directly coupled to the cylindrical part. In some applications, the frustoconical portion of the atrial part is coupled to the cylindrical part via stitching. In some applications, the frustoconical portion of the atrial part is coupled to the cylindrical part via welding. In some applications, the frustoconical portion of the atrial part is coupled to the cylindrical part via gluing.

In some applications, the frustoconical portion of the atrial part is coupled to the cylindrical part, such that the frustoconical portion of the atrial part extends from an axial location along the cylindrical part that is in a lowest 90 percent of a height of the cylindrical part. In some applications, the frustoconical portion of the atrial part is coupled to the cylindrical part, such that the frustoconical portion of the atrial part extends from an axial location along the cylindrical part that is in a lowest 70 percent of the height of the cylindrical part. In some applications, the frustoconical portion of the atrial part is coupled to the cylindrical part, such that the frustoconical portion of the atrial part extends from an axial location along the cylindrical part that is in a lowest 50 percent of the height of the cylindrical part.

In some applications, the valve frame further includes a plurality of chord-recruiting arms configured to extend at least radially from the ventricular end of the cylindrical part.

In some applications, the apparatus further includes a delivery device configured to:

deliver the valve frame to the native atrio-ventricular valve, subsequently, deploy the plurality of chord-recruiting arms among the chords of the native atrio-ventricular valve, and subsequently, rotate at least a portion of the valve frame, such as to cause the plurality of chord-recruiting arms to (a) pull the native atrio-ventricular valve radially inward toward the valve frame, and (b) twist the native atrio-ventricular valve around the valve frame, by recruiting and deflecting at least a portion of the chords.

In some applications, a tip of each of the chord-recruiting arms is rounded such as to guide chords around the tip of the chord-recruiting arm without damaging tissue. In some applications, a tip of each of the chord-recruiting arms is cushioned such as to guide chords around the tip of the chord-recruiting arm without damaging tissue.

In some applications:
the delivery device is configured to deploy the plurality of chord-recruiting arms among the chords of the native atrio-ventricular valve while maintaining the cylindrical part in at least partially radially constrained configuration, such that the chord-recruiting arms assume a rotation configuration in which the chord-recruiting arms extend at least radially from the ventricular end of the cylindrical part, and curve circumferentially around the cylindrical part in a given circumferential direction, and the delivery device is configured to rotate at least the portion of the valve frame, while the chord-recruiting arms are disposed in the rotation configuration.

In some applications, subsequent to rotating at least the portion of the valve frame,
the delivery device is configured to release the atrial part and the cylindrical part of the valve frame, to thereby cause the native atrio-ventricular valve to be held (a) radially inwardly toward the valve frame, and (b) twisted around the valve frame,
by causing at least a portion of the native atrio-ventricular valve to become trapped within the valve frame.

In some applications, when the atrial part and the cylindrical part of the valve frame have been released by the delivery device, the chord-recruiting arms are configured to define pockets, and the pockets defined by the chord-recruiting arms are configured to accommodate the trapped portion of the native atrio-ventricular valve.

In some applications:
the delivery device is configured, initially, to rotate at least the portion of the valve frame in an opposite circumferential direction from the direction of circumferential curvature of the chord-recruiting arms; and
the delivery device is configured, subsequently, to rotate at least the portion of the valve frame in the direction of circumferential curvature of the chord-recruiting arms, such as to cause the plurality of chord-recruiting arms to (a) pull the native atrio-ventricular valve radially inward toward the valve frame, and (b) twist the native atrio-ventricular valve around the valve frame, by recruiting and deflecting at least the portion of the chords.

In some applications, in the rotation configuration of the chord-recruiting arms:
an outer surface of each of the chord-recruiting arms has a smooth, convex curvature that extends along substantially a full length of the chord-recruiting arm, such that during the rotation of at least the portion of the valve frame in the opposite circumferential direction from the direction of circumferential curvature of the chord-recruiting arms, chords slide over the outer surface of the chord-recruiting arm without be recruited or caught by the chord-recruiting arm; and
an inner surface of each of the chord-recruiting arms has a concave curvature, such that during the rotation of at least the portion of the valve frame in the direction of circumferential curvature of the chord-recruiting arms, the chords are recruited within a space defined by the concave curvature.

In some applications, the disc-shaped portion of the atrial part includes struts that define cells, and at least some of the struts have an undulating pattern that are configured to provide the cells of the flange with flexibility, such that the disc-shaped portion is able to adapt its shape to conform with changes in a shape of tissue on the atrial side of the valve annulus.

In some applications, the cells of the disc-shaped portion are curved circumferentially, such that outer tips of the cells point in a given circumferential direction.

In some applications, the valve frame further includes chord-recruiting arms that are configured to curve around the cylindrical part circumferentially in an opposite direction of circumferential curvature from the given circumferential direction.

There is further provided, in accordance with some applications of the present invention, apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus including:
a valve frame configured to support the prosthetic valve within the native atrio-ventricular valve, the valve frame including:
an atrial part including a flange configured to be deployed on an atrial side of the valve annulus, and a frustoconical portion;
a cylindrical part to which the prosthetic valve leaflets are coupled, the cylindrical part configured to be deployed such that a ventricular end of the cylindrical part is disposed within the ventricle,
the flange includes struts that define cells, and at least some of the struts have an undulating pattern that are configured to provide the cells of the flange with flexibility, such that the flange is able to adapt its shape to conform with changes in a shape of tissue on the atrial side of the valve annulus.

In some applications, the cells of the flange are curved circumferentially, such that outer tips of the cells point in a given circumferential direction.

In some applications, the valve frame further includes a plurality of chord-recruiting arms that are configured to extend radially from the ventricular end of the cylindrical part, and that are configured to curve around the cylindrical part circumferentially in an opposite direction of circumferential curvature from the given circumferential direction.

There is further provided, in accordance with some applications of the present invention, apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus including:
a valve frame configured to support the prosthetic valve within the native atrio-ventricular valve, the valve frame including:
an atrial part including a disc-shaped portion configured to be deployed on an atrial side of the valve annulus;
a cylindrical part to which the prosthetic valve leaflets are coupled, the cylindrical part configured to be deployed such that a ventricular end of the cylindrical part is disposed within the ventricle;
a plurality of chord-recruiting arms configured to extend at least radially from the ventricular end of the cylindrical part, the plurality of chord-recruiting arms being configured:
to be deployed among the chords of the native atrio-ventricular valve, while the cylindrical part is maintained in at least partially radially constrained configuration, such that the chord-recruiting arms assume a rotation configuration in which the chord-recruiting arms extend at least radially from the ventricular end of the cylindrical part, and curve circumferentially around the cylindrical part in a given circumferential direction, and in the rotation configuration of the chord-recruiting arms:
an outer surface of each of the chord-recruiting arms has a smooth, convex curvature that extends along substantially a full length of the chord-recruiting arm, such that during rotation of at least the portion of the valve frame in the opposite circumferential direction from the direction of circumferential curvature of the chord-recruiting arms, chords slide over the outer surface of the chord-recruiting arm without be recruited or caught by the chord-recruiting arm; and
an inner surface of each of the chord-recruiting arms has a concave curvature, such that during rotation of at least the portion of the valve frame in the direction of circumferential curvature of the chord-recruiting arms, the chords are recruited within a space defined by the concave curvature.

In some applications, the outer surface of each of the chord-recruiting arms is covered with a low-friction fabric, such as to allow movement of the outer surface with respect to the chords without damaging tissue. In some applications, the inner surface of each of the chord-recruiting arms is covered with a low-friction fabric, such as to allow movement of the inner surface with respect to the chords without damaging tissue. In some applications, a tip of each of the chord-recruiting arms is rounded such as to guide chords around the tip of the chord-recruiting arm without damaging tissue. In some applications, a tip of each of the chord-recruiting arms is cushioned such as to guide chords around the tip of the chord-recruiting arm without damaging tissue.

In some applications, the apparatus further includes a delivery device configured to:
deliver the valve frame to the native atrio-ventricular valve,
subsequently, deploy the plurality of chord-recruiting arms among the chords of the native atrio-ventricular valve, while maintaining the cylindrical part in at least partially radially constrained configuration, such that the chord-recruiting arms assume the rotation configuration, and
while the chord-recruiting arms are disposed in the rotation configuration:
initially rotate at least a portion of the valve frame in an opposite circumferential direction from the direction of circumferential curvature of the chord-recruiting arms; and
subsequently, rotate at least the portion of the valve frame in the direction of circumferential curvature of the chord-recruiting arms, such as to cause the plurality of chord-recruiting arms to (a) pull the native atrio-ventricular valve radially inward toward the valve frame, and (b) twist the native atrio-ventricular valve around the valve frame, by recruiting and deflecting at least the portion of the chords.

In some applications, subsequent to rotating at least the portion of the valve frame, the delivery device is configured to release the atrial part and the cylindrical part of the valve frame, to thereby cause the native atrio-ventricular valve to held (a) radially inwardly toward the valve frame and (b) twisted around the valve frame, by causing at least a portion of the native atrio-ventricular valve to become trapped within the valve frame.

In some applications, when the atrial part and the cylindrical part of the valve frame have been released by the delivery device, the chord-recruiting arms are configured to define pockets, and the pockets defined by the chord-recruiting arms are configured to accommodate the trapped portion of the native atrio-ventricular valve.

There is further provided, in accordance with some applications of the present invention, a method for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the method including:
deploying a valve frame within the native atrio-ventricular valve, by:
deploying an atrial part of the valve frame at least partially within the subject's atrium, the atrial part including a disc-shaped portion configured to be deployed on an atrial side of the valve annulus, and a frustoconical portion;
deploying a cylindrical part of the valve frame such that a ventricular end of the cylindrical part is disposed within the subject's ventricle, the prosthetic valve leaflets being coupled to the cylindrical part,
a plurality of protruding struts protruding from outside the cylindrical part, the frustoconical portion of the atrial part being coupled to the cylindrical part via the protruding struts.

There is further provided, in accordance with some applications of the present invention, a method for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the method including:
deploying a valve frame within the native atrio-ventricular valve, by:
deploying an atrial part of the valve frame at least partially within the subject's atrium, the atrial part including a disc-shaped portion configured to be deployed on an atrial side of the valve annulus, and a frustoconical portion;
deploying a cylindrical part of the valve frame such that a ventricular end of the cylindrical part is disposed within the subject's ventricle, the prosthetic valve leaflets being coupled to the cylindrical part,
the frustoconical portion of the atrial part being coupled to the cylindrical part, such that there is axial overlap between at least the frustoconical portion of the atrial part and the cylindrical part.

There is further provided, in accordance with some applications of the present invention, apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus including:
   a valve frame configured to support the prosthetic valve within the native atrio-ventricular valve, the valve frame including:
      an atrial part including a disc-shaped portion configured to be deployed on an atrial side of the valve annulus;
      a cylindrical part to which the prosthetic valve leaflets are coupled, the cylindrical part configured to be deployed such that a ventricular end of the cylindrical part is disposed within the ventricle;
      a plurality of chord-recruiting arms configured to extend at least radially from the ventricular end of the cylindrical part, the chord-recruiting arms being configured to deploy among the chords of the native atrio-ventricular valve, and, in response to the valve frame being rotated in a given direction, to (a) pull the native atrio-ventricular valve radially inward toward the valve frame, and (b) twist the native atrio-ventricular valve around the valve frame, by recruiting and deflecting at least a portion of the chords; and
      a plurality of anti-recoil elements extending from the disc-shaped portion of the atrial part of the valve frame, the anti-recoil elements being configured to prevent rotation of the valve frame in the opposite direction to the direction in which the valve frame was rotated.

There is further provided, in accordance with some applications of the present invention, a method for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the method including:
   placing a valve frame within the native atrio-ventricular valve, the valve frame including:
      an atrial part configured to be deployed on an atrial side of the valve annulus,
      a cylindrical part to which the prosthetic valve leaflets are coupled, the cylindrical part configured to be deployed such that a ventricular end of the cylindrical part is disposed within the subject's ventricle, and
      a plurality of chord-recruiting arms configured to extend at least radially from the ventricular end of the cylindrical part;
   causing the chord-recruiting arms to deploy among the chords of the native atrio-ventricular valve;
   rotating the valve frame in a given direction, such to (a) pull the native atrio-ventricular valve radially inward toward the valve frame, and (b) twist the native atrio-ventricular valve around the valve frame, by recruiting and deflecting at least a portion of the chords; and
   deploying anti-recoil elements into tissue of the subject's atrium, such as to prevent rotation of the valve frame in the opposite direction to the direction in which the valve frame was rotated.

There is further provided, in accordance with some applications of the present invention, apparatus for use with a delivery device and with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus including:
   a valve frame configured to support the prosthetic valve within the native atrio-ventricular valve, the valve frame including:
      an atrial part including a disc-shaped portion configured to be deployed on an atrial side of the valve annulus;
      a cylindrical part to which the prosthetic valve leaflets are coupled, the cylindrical part configured to be deployed such that a ventricular end of the cylindrical part is disposed within the ventricle;
      a plurality of chord-recruiting arms configured to extend at least radially from the ventricular end of the cylindrical part,
   the valve frame including lever elements extending from the chord-recruiting arms, the lever element being configured such that when the chord-recruiting arms are deployed among the chords of the native atrio-ventricular valve, and the lever elements are held within the delivery device, the lever elements cause the chord-recruiting arms to pivot radially outwards.

There is further provided, in accordance with some applications of the present invention, a method for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the method including:
   delivering a valve frame to the native atrio-ventricular valve using a delivery device, the valve frame including:
      an atrial part configured to be deployed on an atrial side of the valve annulus,
      a cylindrical part to which the prosthetic valve leaflets are coupled, the cylindrical part configured to be deployed such that a ventricular end of the cylindrical part is disposed within the subject's ventricle,
      a plurality of chord-recruiting arms configured to extend at least radially from the ventricular end of the cylindrical part, and
      lever elements extending from the chord-recruiting arms;
   causing the chord-recruiting arms to deploy among the chords of the native atrio-ventricular valve, at least partially by holding lever elements within the delivery device, such as to cause the chord-recruiting arms to pivot radially outwardly; and
   rotating the valve frame in a given direction, such to (a) pull the native atrio-ventricular valve radially inward toward the valve frame, and (b) twist the native atrio-ventricular valve around the valve frame, by recruiting and deflecting at least a portion of the chords.

There is further provided, in accordance with some applications of the present invention, a method for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the method including:
   delivering a valve frame to the native atrio-ventricular valve using a delivery device, the valve frame including:
      an atrial part configured to be deployed on an atrial side of the valve annulus, a cylindrical part to which the prosthetic valve leaflets are coupled, the cylindrical part configured to be deployed such that a ventricular end of the cylindrical part is disposed within the subject's ventricle, a plurality of chord-recruiting arms configured to extend at least radially from the ventricular end of the cylindrical part, the chord-recruiting arms being coupled to the ventricular end of the cylindrical part via stitches;

causing the chord-recruiting arms to deploy among the chords of the native atrio-ventricular valve, by releasing the chord-recruiting arms from the delivery device, such that the chord-recruiting arms extend radially outwardly by pivoting about the stitches with respect to the cylindrical part; and rotating the valve frame in a given direction, such to (a) pull the native atrio-ventricular valve radially inward toward the valve frame, and (b) twist the native atrio-ventricular valve around the valve frame, by recruiting and deflecting at least a portion of the chords.

There is further provided, in accordance with some applications of the present invention, a method for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the method including:

delivering a valve frame to the native atrio-ventricular valve using a delivery device, the valve frame including:

an atrial part configured to be deployed on an atrial side of the valve annulus, a cylindrical part to which the prosthetic valve leaflets are coupled, the cylindrical part configured to be deployed such that a ventricular end of the cylindrical part is disposed within the subject's ventricle, a plurality of chord-recruiting arms configured to extend at least radially from the ventricular end of the cylindrical part, and configured to curve with respect to a longitudinal axis of the valve frame in a given direction of circumferential curvature;

causing the chord-recruiting arms to deploy among the chords of the native atrio-ventricular valve, by releasing the chord-recruiting arms from the delivery device;

subsequently, rotating the valve frame circumferentially in the opposite direction to the direction of direction of circumferential curvature of the chord-recruiting arms; and further subsequently, rotating the valve frame circumferentially in the direction of circumferential curvature of the chord-recruiting arms such to (a) pull the native atrio-ventricular valve radially inward toward the valve frame, and (b) twist the native atrio-ventricular valve around the valve frame, by recruiting and deflecting at least a portion of the chords.

The present invention will be more fully understood from the following detailed description of applications thereof, taken together with the drawings, in which:

DETAILED DESCRIPTION OF EMBODIMENTS

Figure 1A:
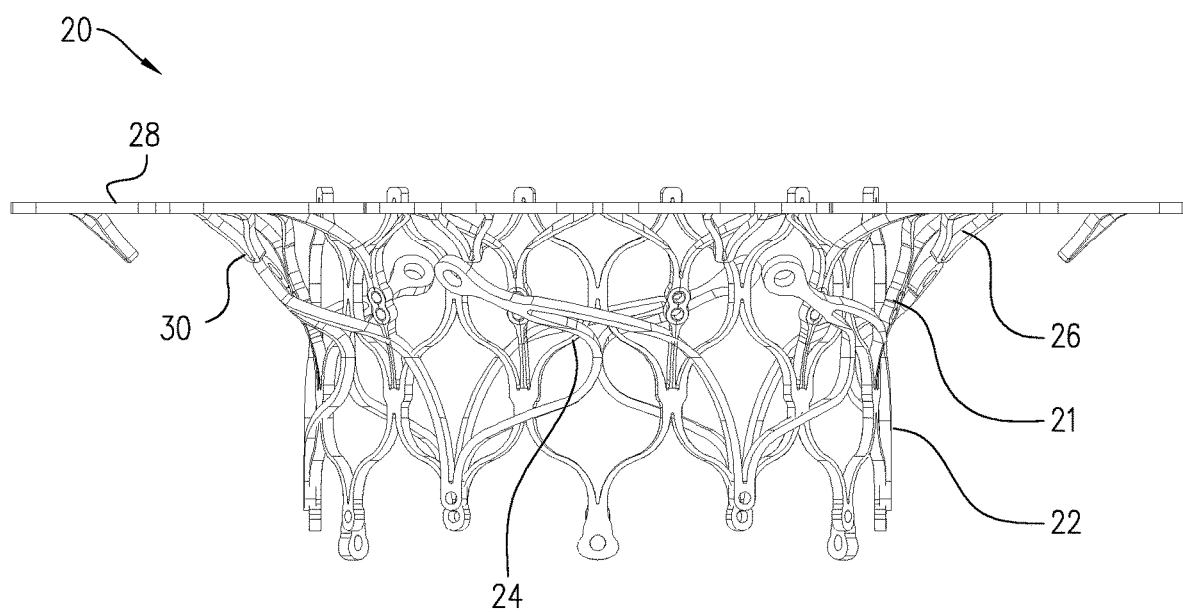
FIGS. 1A, 1B, and 1C are schematic illustrations of respective views of a valve frame that is configured to support a prosthetic valve within a subject's native atrio-ventricular valve, the figures showing the valve frame disposed in a non-radially-constrained configuration, in accordance with some applications of the present invention.
Figure 1B:
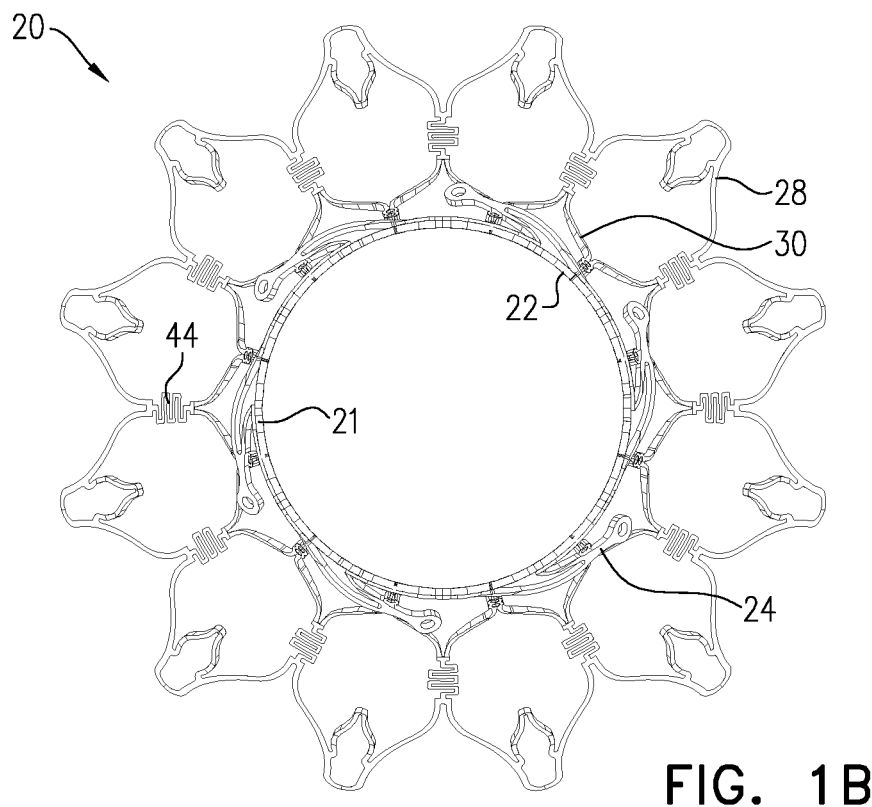
Figure 1C:
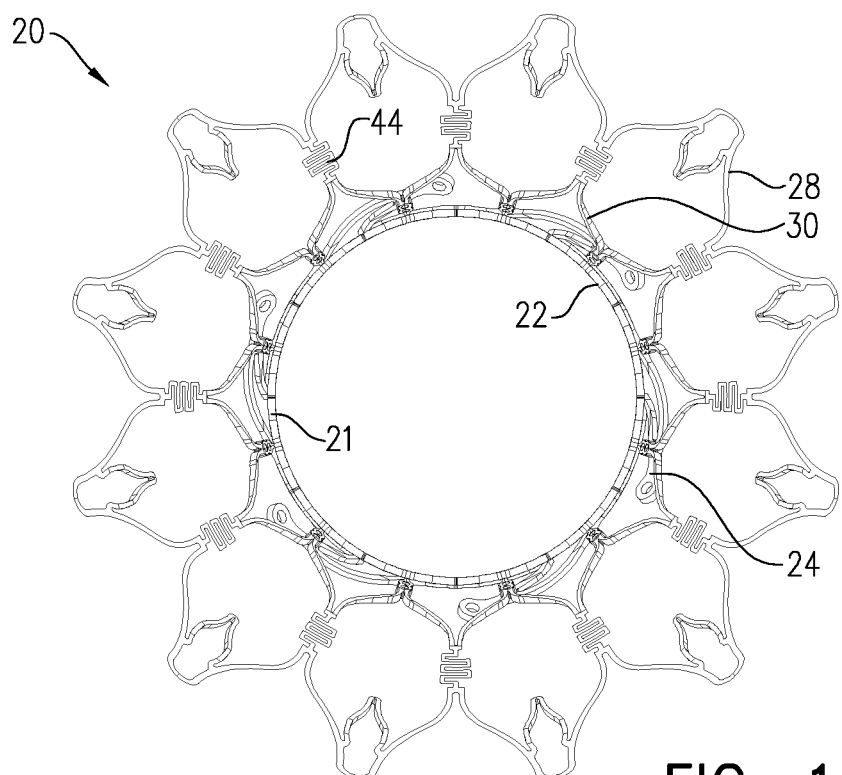
Figure 1D:
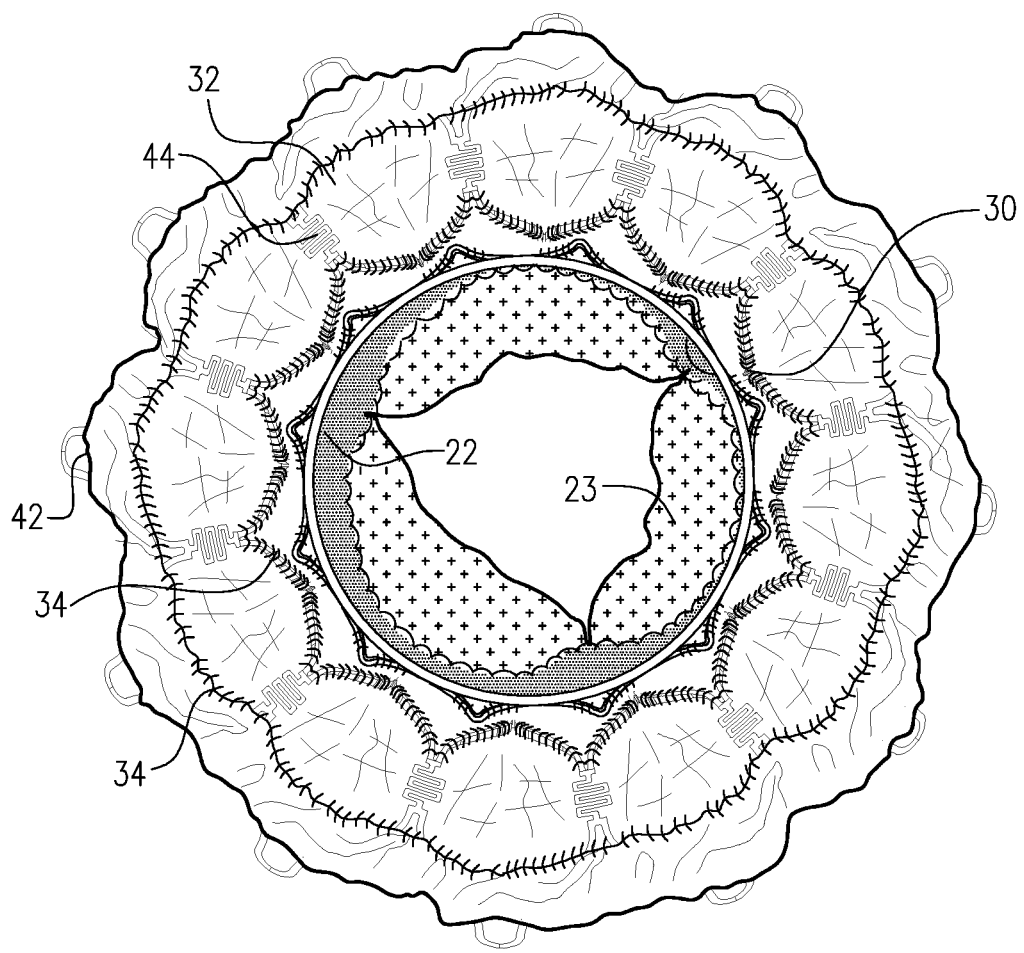
FIG. 1D is a schematic illustration of the valve frame of FIGS. 1A, 1B, and 1C, in a non-radially-constrained configuration, showing valve leaflets and covering material attached to the valve frame, in accordance with some applications of the present invention.

Reference is now made to FIGS. 1A, 1B, and 1C, which are schematic illustrations of respective views of a valve frame 20, the figures showing the valve frame in its non-radially-constrained configuration, in accordance with some applications of the present invention. FIG. 1A shows a side view of the valve frame, FIG. 1B shows a bottom view (i.e., a view from a ventricular end of the valve frame), and FIG. 1C shows a top view (i.e., a view from an atrial end of the valve frame). Reference is also made to FIG. 1D, which is a schematic illustration of valve frame 20, with valve leaflets 23 coupled to the valve frame, in accordance with some applications of the present invention.

Typically, the valve frame includes a valve-frame body 21. For some applications, valve-frame body 21 includes a cylindrical part 22, as well as an atrial part 26. Typically, the cylindrical part is configured to support the prosthetic valve within the native atrio-ventricular valve. For example, leaflets 23 of the prosthetic valve may be sutured to the cylindrical part, and/or may be otherwise coupled to the cylindrical part, e.g., as shown in FIG. 1D. Typically, atrial part 26 is configured to be deployed at least partially within the subject's atrium. For some applications, atrial part 26 includes a disc-shaped portion 28 (also referred to herein as a flange) and a frustoconical portion 30.

Typically, the disc-shaped portion of the atrial part is configured to seal the valve frame with respect to tissue on the atrial side of the mitral annulus, and is further configured to prevent migration of the valve frame into the left ventricle. The frustoconical portion typically extends from the disc-shaped portion of the atrial part to the outer surface of the cylindrical part. For some applications, the inclusion of the frustoconical portion between the disc-shaped portion and the cylindrical part (as opposed to directly coupling the disc-shaped portion to the cylindrical part) reduces a likelihood of regurgitation around the outside of the cylindrical part.

For some applications, the cylindrical part and the atrial part are formed as separate pieces from one another and are coupled to each other, for example, via stitching, gluing, welding, and/or another method. Alternatively, the cylindrical part and the atrial part are portions of a single integrally-formed piece, e.g., as described hereinbelow with reference to FIGS. 8A-C.

Typically, valve frame 20 is made of a shape-memory material (e.g., a shape-memory alloy, such as nitinol and/or copper-aluminum-nickel), which is covered on one or both sides with a covering material 32 (shown in FIG. 1D), e.g., a fabric and/or a polymer (such as expanded polytetrafluoroethylene (ePTFE), or woven, knitted, mesh and/or braided polyester). Typically, the shape-memory material of cylindrical part 22 and atrial part 26 is shaped into a stent-like structure that comprises struts and/or cells of the shape-memory material. The covering material is typically coupled to the shape-memory material via stitches 34 (shown in FIG. 1D). It is noted that FIGS. 1A-C (as well as FIGS. 3A-10B) show valve frame 20 in the absence of valve leaflets 23 and covering material 32 for illustrative purposes. However, valve leaflets 23, and covering material 32 may be observed in FIG. 1D.

For some applications, a plurality of chord-recruiting arms 24 (e.g., more than two and/or fewer than twelve arms) extend from a portion of valve-frame body 21 that is configured to be placed within the subject's ventricle. For example, four chord-recruiting arms or six chord-recruiting arms may extend from the valve-frame body. For some applications, a single chord-recruiting arm 24 extends from a portion of valve-frame body 21 that is configured to be placed within the subject's ventricle. Typically, the chord-recruiting arms extend from cylindrical part 22 of valve-frame body 21. Further typically, the chord-recruiting arms extend from a ventricular end of the cylindrical part (i.e., the end of the valve frame body that is configured to be placed within the ventricle). Typically, in a non-radially constrained configuration of the valve frame (which the valve frame typically assumes when neither the valve frame body nor the chord-recruiting arms are constrained by the delivery device), the arms extend radially from the valve-frame body, in addition to extending axially from the ventricular end of the valve-frame body toward an atrial end of the valve-frame body (i.e., the end of the valve frame body that is configured to be placed within the atrium). Further typically, the arms curve around outside of the valve-frame body in a given circumferential direction of curvature.

As noted in the Summary section, descriptions herein of the arms extending from the valve-frame body in a given direction should not be interpreted as excluding additional directions in which the arms are oriented. Rather, the arms being described (or claimed) as extending radially from the valve-frame body should be interpreted as meaning that the orientation of the arms with respect to the valve-frame body includes a radial component. It is typically the case that, in addition to extending radially from the valve-frame body, the arms curve circumferentially, and in some cases the orientation of the arms includes an axial component. For some applications, at least along a portion of the arms, and at least in certain configurations of the arms, the arms are disposed tangentially with respect to the valve-frame body.

Typically, valve frame 20 with prosthetic valve leaflets 23 disposed therein is delivered to the native atrio-ventricular valve, via a delivery device 40 (e.g., a delivery catheter, shown in FIG. 2), and the delivery device is configured to maintain the valve frame and the prosthetic valve in radially-constrained configurations (i.e., "crimped" configurations) during the delivery. In accordance with respective applications, the valve frame is delivered transapically (i.e., via the apex of the left ventricle), transseptally (i.e., via the vena cava, the right atrium, and the interatrial septum, as described in detail with reference to FIGS. 11A-F), and/or via a different delivery path. For some applications, when a distal end of the delivery device is disposed within the subject's ventricle, chord-recruiting arms 24 are deployed among chords of the native atrio-ventricular valve. Typically, the chord-recruiting arms are deployed among chords of the native atrio-ventricular valve by releasing the chord-recruiting arms from the delivery device, the chord-recruiting arms being shape set to extend from the valve-frame body, upon being released from the delivery device. For some applications, additional techniques are used in order to cause the chord-recruiting arms to become deployed among chords of the native atrio-ventricular valve by releasing the chord-recruiting arms from the delivery device. For example, the valve frame may include lever elements, which are configured to cause the chord-recruiting arms to extend radially (e.g., as described hereinbelow with reference to FIGS. 7A-B). Alternatively or additionally, the arms are coupled to the cylindrical part of the valve frame via stitches, the stitches acting as hinges, such that the arms pivot about the stitches with respect to the cylindrical part, as described hereinbelow. Typically, the chord-recruiting arms are released from the delivery device while the valve-frame body is still maintained in an at least partially radially-constrained configuration by the delivery device. Typically, the valve frame is rotated while the chord-recruiting arms and the valve-frame body are configured in the aforementioned configuration. Therefore, in the present application, the configuration of the chord-recruiting arms when the valve-frame body is still maintained in an at least partially radially-constrained configuration by the delivery device but the chord-recruiting arms have been released from the delivery device is referred to as the "rotation configuration" of the chord-recruiting arms.

Figure 2A:
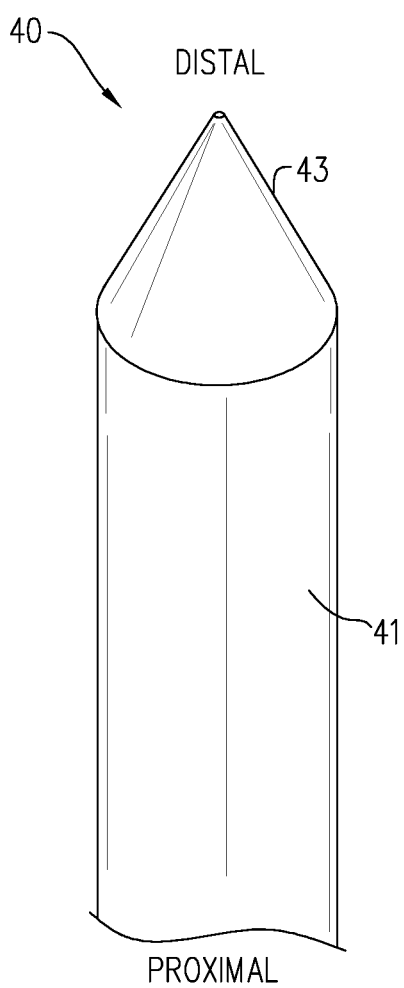
FIGS. 2A and 2B are schematic illustrations of the valve frame of FIGS. 1A, 1B, and 1C fully disposed inside a delivery device (FIG. 2A), and with chord-recruiting arms of the valve frame in "rotation configurations" (FIG. 2B), in accordance with some applications of the present invention.
Figure 2B:
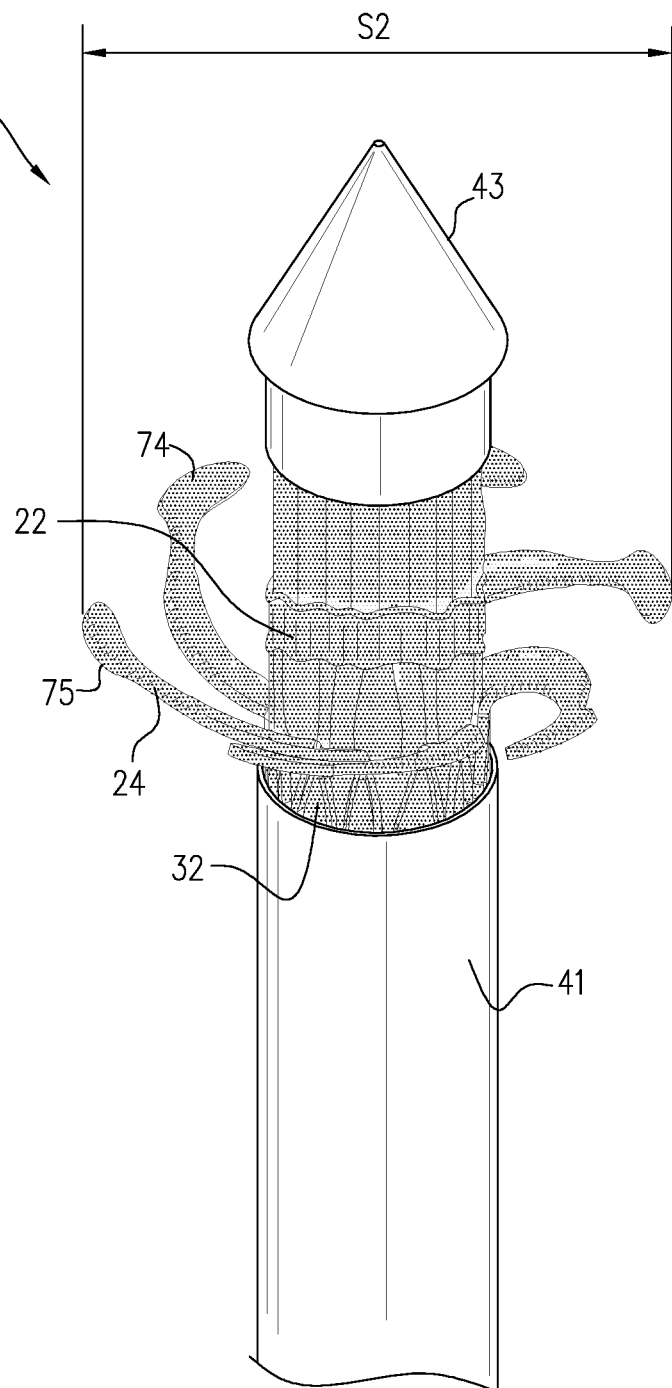

Reference is now made to FIGS. 2A and 2B. FIG. 2A is a schematic illustration of valve frame 20 fully disposed within a delivery device 40, the delivery device typically including a proximal overtube 41 and a nosecone 43, in accordance with some applications of the present invention. FIG. 2B is a schematic illustration of valve frame 20, when the chord-recruiting arms are disposed in their rotation configuration (i.e., when chord-recruiting arms 24 of the valve frame have been released from a delivery device 40 while valve-frame body 21 of the valve frame is still maintained in an at least partial radially-constrained configuration by the delivery device), in accordance with some applications of the present invention. It is noted that FIG. 2B shows the delivery device and the arms configured for insertion from below the mitral valve (e.g., via transapical insertion). For some such applications, in their rotation configuration, the arms extend axially from the distal end of the delivery device in the distal direction (i.e., the end of the delivery device that is further from the insertion point of the delivery device into the subject's body), as shown. For some applications in which the delivery device is inserted from above the mitral valve (e.g., via transseptal insertion, as described in detail hereinbelow with reference to FIGS. 11A-F), in their rotation configuration, the arms extend axially from the distal end of the delivery device in the proximal direction (i.e., back toward the proximal end of the delivery device). For some applications, in their rotation configuration, the chord-recruiting arms are configured to extend radially from valve frame and to curve circumferentially around the valve frame, but not to extend axially in either the proximal or the distal direction. Rather, for such applications, in their rotation configuration, the arms extend from the valve frame in the radial direction with the arms disposed in a single plane along the axial direction.

Subsequent to chord-recruiting arms 24 being deployed among chords of the native atrio-ventricular valve (and typically while valve-frame body 21 is still maintained in the at least partially radially-constrained configuration by the delivery device, as shown in FIG. 2), at least a portion of valve frame 20 is rotated, such as to cause chord-recruiting arms 24 to (a) pull the native atrio-ventricular valve radially inward toward the valve frame, and (b) twist the native atrio-ventricular valve around the valve frame, by recruiting and deflecting at least a portion of the chords. For some applications, the valve frame is rotated during ventricular systole, when the native atrio-ventricular valve is closed, such that the rotation occurs when the chords are closest to the valve frame. Alternatively, the valve frame is rotated irrespective of the phase of the subject's cardiac cycle (i.e., without attempting to synchronize the rotation with a particular phase of the subject's cardiac cycle).

Subsequent to the rotation of the valve-frame, cylindrical part 22 and atrial part 26 are typically allowed to radially expand, e.g., by releasing the cylindrical part and the atrial part from the delivery device, such that the valve frame assumes its non-radially constrained configuration. Typically, the valve frame is configured to thereby trap the native valve leaflets in a partially closed and twisted configuration, to thereby at least partially seal a space between the native atrio-ventricular valve and the prosthetic valve. For example, the cylindrical part may be configured to radially expand such as to trap the native valve leaflets between the cylindrical part and the chord-recruiting arms, and/or the atrial part may be configured to radially expand such as to trap the native valve leaflets between the atrial part and the chord-recruiting arms.

Typically, the chord-recruiting arms 24 are configured to curve in a given circumferential direction with respect to the longitudinal axis of the valve frame, both when the arms are deployed among the chords (i.e., when the arms are disposed in their rotation configuration), and when the cylindrical part 22 and atrial part 26 are allowed to radially expand (i.e., the valve frame assumes its non-radially constrained configuration), as described in further detail hereinbelow. For example, the arms may curve in a clockwise direction or in a counter-clockwise direction with respect to the longitudinal axis of the valve frame. Typically, subsequent to chord-recruiting arms 24 being deployed among chords of the native atrio-ventricular valve (and typically while valve-frame body 21 is still maintained in the at least partially radially-constrained configuration by the delivery device (i.e., when the arms are disposed in their rotation configuration), as shown in FIG. 2), the valve frame is rotated in the same circumferential direction as the direction of the circumferential curvature of the arms. For some applications, prior to rotating the valve frame in this direction, the valve frame is rotated in the opposite circumferential direction. For example, if the arms curve in the clockwise circumferential direction, then, subsequent to the arms being deployed among the chords, the valve frame may first be rotated in the counterclockwise direction and may subsequently be rotated in the clockwise direction. For some applications, rotating the valve frame in this manner facilitates recruitment of a greater portion of the chords than if the valve frame were to only be rotated in the direction of circumferential curvature of the arms.

As described in the above paragraph, for some applications, prior to rotating the valve frame in the same circumferential direction as the direction of the circumferential curvature of the arms, the valve frame is rotated in the opposite circumferential direction. For some applications, the delivery device is configured such as to perform the initial rotation of the valve frame through a given angle against the direction of circumferential curvature of the arm, and to subsequently rotate the valve frame though a predetermined angle in the direction of the circumferential curvature of the arms. For some applications, in the rotation configuration of the chord-recruiting arms, the outer surfaces of each of the arms has a smooth, convex curvature that extends along substantially the full length of the arm, such that during the initial rotation (against the direction of circumferential curvature of the arm) the chords slide over the outer surfaces of the arm without being recruited or caught by the arm. For some applications, by virtue of the arms being shaped in this manner, the initial rotation of the valve frame causes a relatively large number of chords to be positioned such as to be recruited by each of the arms in the subsequent rotation step. During the subsequent rotation of the valve frame (in the direction of the circumferential curvature of the arms), the chords are recruited and deflected by the arms. Typically, in the rotation configuration of the chord-recruiting arms, the inner surface of each of the arms has a concave curvature and the chords are recruited within the space defined by the concave curvature, during the subsequent rotation by the valve frame.

Referring again to FIG. 1D, for some applications, covering material 32 defines slits 42. Typically, when valve frame 20 is arranged in its radially-constrained configuration inside the delivery device, cells of the valve frame become axially elongated. For some applications, slits 42 are configured such as to allow the cells of the valve frame to become axially elongated without tearing the covering material, by the axially-elongated cells extending through the slits. Typically, upon the valve frame being released from the delivery device, and assuming its non-radially constrained configuration, the cells become reinserted into the slits, such as to become covered by the covering material. It is noted that, for illustrative purposes, in FIG. 1D, the tip of the cells are shown as protruding from the slits even in the non-radially-constrained configuration of the valve frame.

Figure 3A:
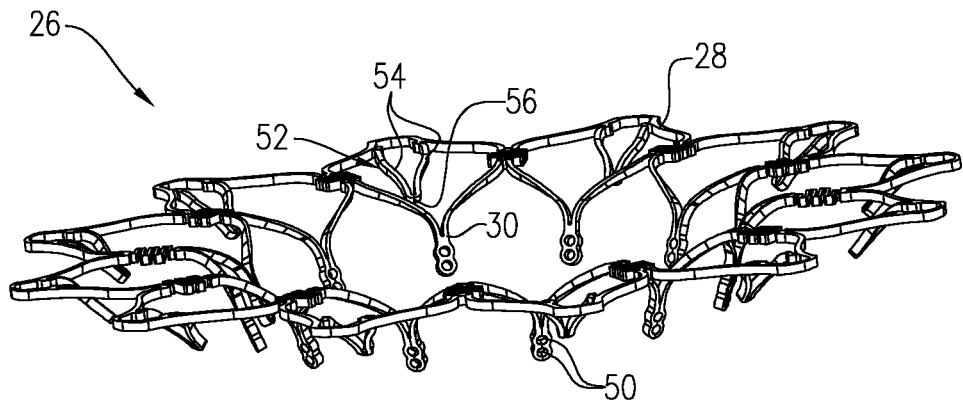
FIGS. 3A and 3B are schematic illustrations of respective views of an atrial part of a valve frame, in accordance with some applications of the present invention.
Figure 3B:
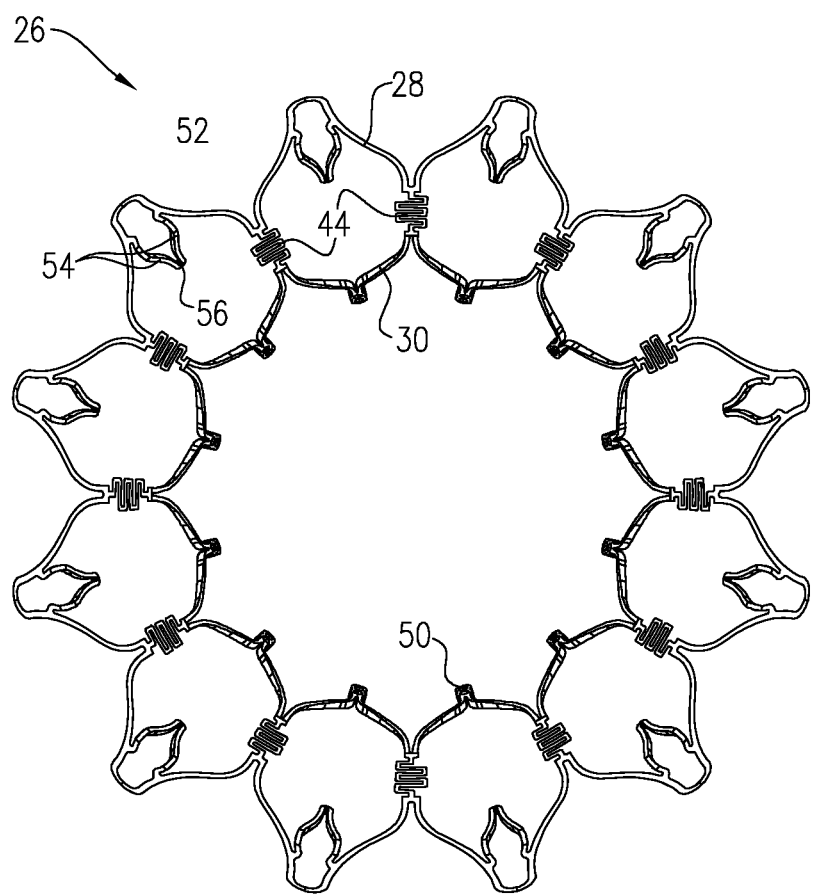

Reference is now made to FIGS. 3A and 3B, which are schematic illustrations of respective views of atrial part 26, in accordance with some applications of the present invention. FIG. 3A shows a three-dimensional side view, and FIG. 3B shows a top view. As described hereinabove, typically, atrial part 26 is configured to be deployed at least partially within the subject's atrium. For some applications, atrial part 26 includes a disc-shaped portion 28 (also referred to herein as a flange) and a frustoconical portion 30. The disc-shaped portion is typically configured to be placed upon the native mitral valve annulus, and the frustoconical portion extends from the disc-shaped portion of the atrial part to cylindrical part 22. Typically, the disc-shaped portion of the atrial part is configured to seal the valve frame with respect to tissue on the atrial side of the mitral annulus, and is further configured to prevent migration of the valve frame into the left ventricle. For some applications, cells of the flange include spring portions 44. The spring portions are configured to provide the cells with flexibility, such that the flange is able to adapt its shape to conform with changes in the shape of the atrial tissue that the flange contacts, during movement of the heart. Alternatively or additionally, the cells of the flange are provided with flexibility by virtue of struts of the cells themselves having an undulating pattern, as described in further detail hereinbelow with reference to FIGS. 10A-B. For some applications, the inclusion of the frustoconical portion between the disc-shaped portion and the cylindrical part (as opposed to directly coupling the disc-shaped portion to the cylindrical portion) reduces a likelihood of regurgitation around the outside of the cylindrical part. It is noted that, in accordance with respective applications, the flange is disposed within a plane that is perpendicular to the longitudinal axis defined by the cylindrical part, or is disposed at an angle to such a plane. For example, the flange may define an upwards angle or a downwards angle with respect to a plane that is perpendicular to the longitudinal axis defined by the cylindrical part, to best match the different anatomical structures surrounding the native atrioventricular valves, either in the atrium or ventricle.

For some applications, the frustoconical portion defines holes 50 at the bottom of at least some of the cells of the frustoconical portion. Typically the holes are configured to facilitate stitching of the atrial part to the cylindrical part of the valve frame. For some applications, pairs 52 of struts 54 extend from respective cells of disc-shaped portion 28 of the atrial part. The pairs of struts converge to a point 56. For some applications, pairs of struts are configured to pierce tissue of the subject's heart (e.g., tissue of the valve annulus) at point 56. As described hereinabove, typically, the valve frame is rotated in order to recruit chords of the native valve, and, subsequently, the valve-frame body is allowed to radially expand. In some cases, the valve frame has a tendency to undergo recoil and to rotate in the opposite direction to the direction in which it was rotated. Typically, by piercing tissue of the subject's heart at point 56 (and then becoming embedded within the tissue), the pairs of struts are configured to act as anti-recoil elements by preventing rotation of the valve frame in the opposite direction to the direction in which it was rotated.

Figure 4A:
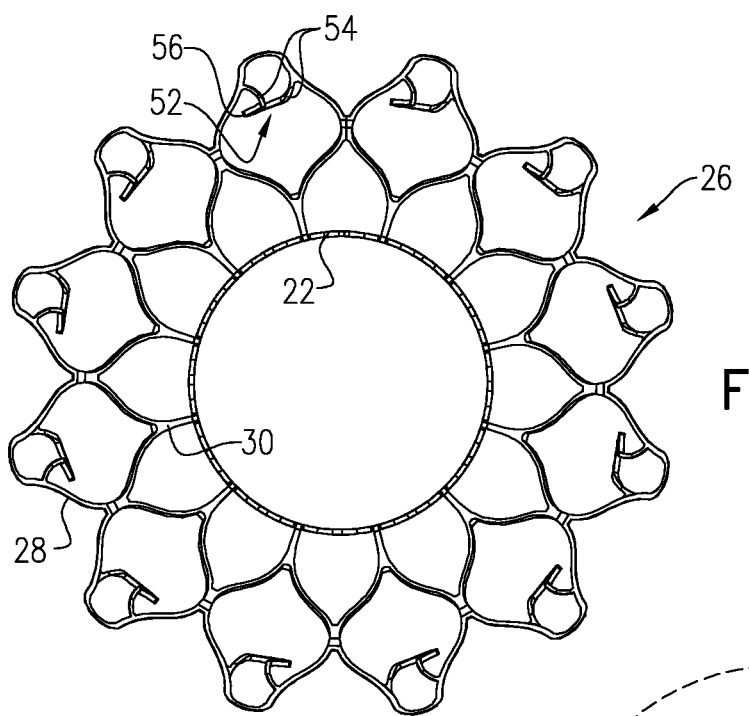
FIGS. 4A and 4B are schematic illustrations of top views of atrial and cylindrical parts of a valve frame, in accordance with respective applications of the present invention.
Figure 4B:
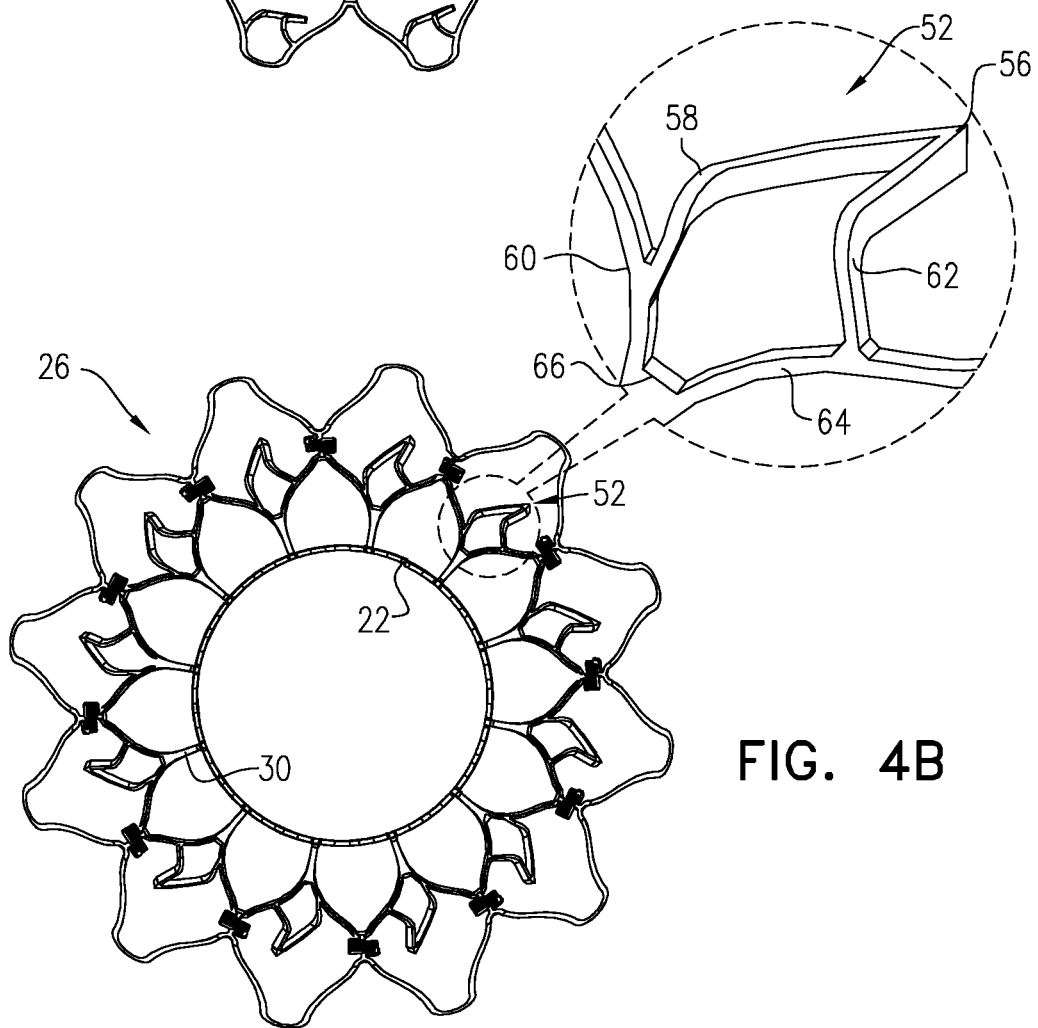

Reference is now made to FIGS. 4A and 4B, which are schematic illustrations of top views of atrial part 26 and cylindrical part 22, in accordance with respective applications of the present invention. As described with reference to FIGS. 3A and 3B, for some applications, pairs 52 of struts 54 extend from respective cells of disc-shaped portion 28 of the atrial part. Typically, the pairs of struts are configured to act as anti-recoil elements by preventing rotation of the valve frame in the opposite direction to the direction in which it was rotated. For some applications, the pairs of struts additionally facilitate anchoring of the atrial part to the native tissue.

As shown in FIG. 4A, for some applications the pairs of struts are curved with respect to the axis of the valve frame, in a circumferential direction. Typically, the curvature of the pairs of struts is configured to facilitate the anti-recoil functionality, by the struts curving to face the direction in which the valve frame has a tendency to rotate. For example, in the example shown in FIG. 4A, the valve frame is configured to initially be rotated in a clockwise direction (when viewed from on top, as shown in FIG. 4A). In some cases, the valve frame therefore has a tendency to recoil and to rotate in the counterclockwise direction. The curvature of the pairs of struts is such that as the valve frame begins to rotate in the counterclockwise direction, points 56 of pairs 52 of struts 54 pierce the tissue of the subject's heart (and become at least partially embedded within the tissue), thereby opposing further rotation of the valve frame.

Typically, each strut 54 of a given pair 52 is configured to extend from a strut of a respective side (i.e., a left-side or a right side) of a cell of disc-shaped portion 28 of the atrial part. As shown in FIG. 4A, for some applications, each strut 54 of a given pair 52 is configured to extend from a strut of a respective side of an outer half of a cell of disc-shaped portion 28 of the atrial part. Alternatively, as shown in FIG. 4B, each strut 54 of a given pair 52 is configured to extend from a strut of a respective side (i.e., a left-side or a right side) of an inner half of a cell of disc-shaped portion 28 of the atrial part.

For some applications, in addition to being curved (as described with reference to FIG. 4A), pairs 52 of struts 54 are twisted with respect to the cell from which they extend. For example, as shown in FIG. 4B, strut 58 is connected to strut 60, which is on the inner left side of a cell of the disc-shaped portion 28 of the atrial part. Strut 62 is connected to strut 64, which is on the inner right side of a cell of the disc-shaped portion 28 of the atrial part. Struts 60 and 64 form a junction 66 with each other. Strut 58 is connected to strut 60 at a location that is closer to junction 66 than the location of the connection between strut 62 with strut 64. This results in the pair 52 of struts 58 and 62 being twisted with respect to the disc-shaped portion 28 of the atrial part. For some applications, the twistedness of pairs 52 of struts is configured to facilitate the anti-recoil functionality of the pairs of struts, by the struts becoming more embedded within tissue of the subject's heart (in response to the valve frame starting to undergo recoil) than if the struts were not to have the twisted configuration. For some applications, valve frame 20 does not include anti-recoil elements, as described with reference to FIGS. 4A-B.

Figure 5A:
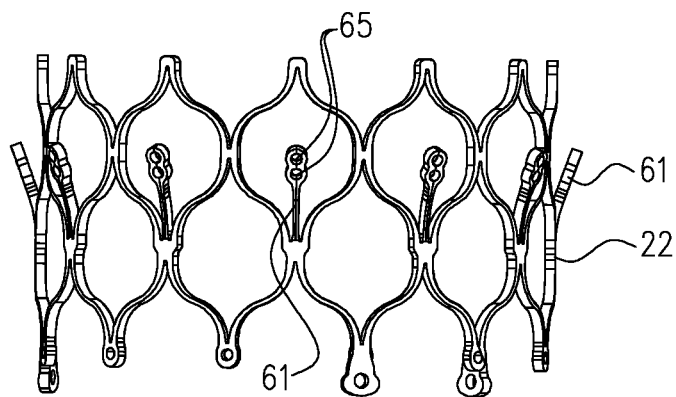
FIG. 5A is a schematic illustration of a side view of a cylindrical part of a valve frame in accordance with some applications of the present invention.
Figure 5B:
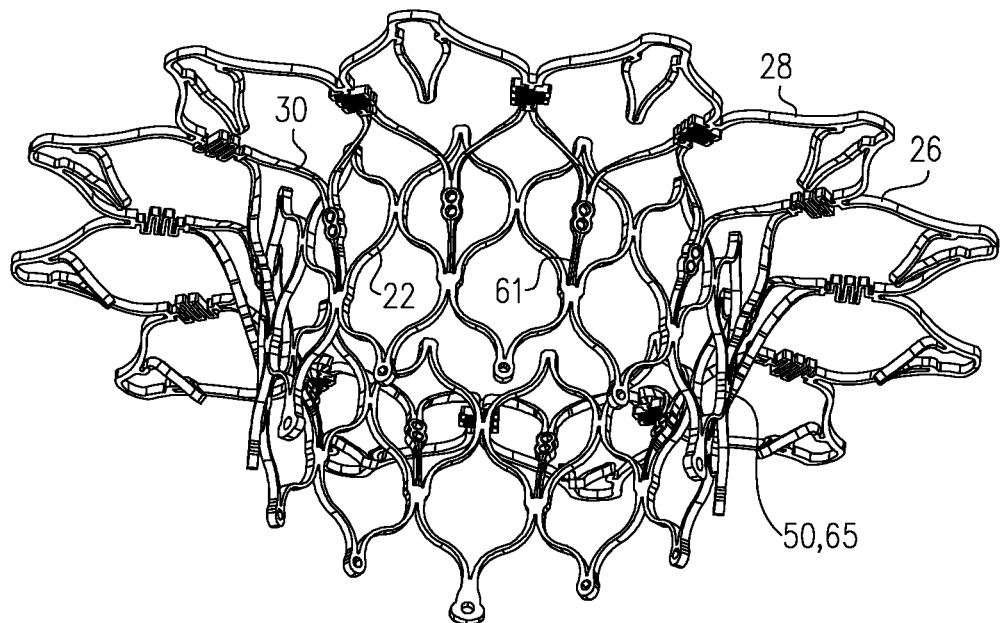
FIG. 5B is a schematic illustration of an atrial part of a valve frame coupled to a cylindrical part of the valve frame, in accordance with some applications of the present invention.

Reference is now made to FIG. 5A, which is a schematic illustration of a side view of cylindrical part 22, in accordance with some applications of the present invention. Reference is also made to FIG. 5B, which is a schematic illustration of atrial part 26 coupled to cylindrical part 22, in accordance with some applications of the present invention. For some applications, a plurality of struts 61 protrude from the outside of cylindrical part 22. For some applications, the protrusion of the struts from the outside of cylindrical part 22 is such that the orientation of the struts with respect to the cylindrical part has an a radial and an axial component. For some applications, along at least a portion of the struts, the struts are disposed tangentially with respect to the cylindrical part. Typically, the atrial part is coupled to the cylindrical part by the atrial part being coupled to protruding struts 61. For example, as described hereinabove, frustoconical portion 30 of atrial part 26 may define holes 50 at the bottom of at least some of the cells of the frustoconical portion. For some applications, protruding struts 61 also define holes 65, and the atrial part is coupled to the cylindrical part by stitching sutures through holes 50 defined by the atrial part and corresponding holes 65 defined by protruding struts 61 of cylindrical part 22. Alternatively or additionally, the atrial part is coupled to the protruding struts via other means, e.g., via welding (such as laser welding), gluing, and/or a different method.

It is noted that, typically, during the crimping of the valve frame, there is a lot of strain that is placed on the junctions from which protruding struts 61 protrude from the cylindrical part, since the struts pivot about these junctions. If the atrial part were to be directly coupled to the cylindrical part at these junctions, then this would mean that these points at which there is relatively large strain placed on the valve frame are also points at which the two pieces are coupled to each other, which would make the frame susceptible to fatigue at these points. By contrast, by virtue of the cylindrical part including protruding struts 61 and the atrial part being coupled to the cylindrical part via the struts, there is a separation between the points of high strain and the points at which atrial part is coupled to the cylindrical part.

It is further noted that typically, the protruding struts protrude from an axial location along the cylindrical part that is in the lowest 90 percent (e.g., the lowest 70 percent, or the lowest 50 percent) of the height of the cylindrical part. Typically, the cylindrical part has a height of at least 15 mm, in order to accommodate the coupling of the valve leaflets to the cylindrical part. If the protruding struts were to protrude from the top of the cylindrical part (or if the atrial part were to be coupled directly to the cylindrical part at the top of the cylindrical part), then the entire height of the cylindrical part would be disposed below the atrial part. By contrast, since the protruding struts protrude from the lowest 90 percent (e.g., the lowest 70 percent, or the lowest 50 percent) of the height of the cylindrical part, there is typically axial overlap between the atrial part and the cylindrical part of the valve frame, along the height of the cylindrical part. Typically, this results in a smaller portion of the height of the cylindrical part protruding into the subject's ventricle, then if there were to be no axial overlap between the atrial part and the cylindrical part of the valve frame (which poses less restriction on the ventricle, by reducing the ventricular presence of the cylindrical part). In turn (when valve frame 20 is configured for placement within the subject's left ventricle), this typically reduces obstruction of the left ventricular outflow tract, relative to if a larger portion of the height of the cylindrical part were to protrude into the subject's ventricle. In this context, it is noted that, as described hereinabove, chord-recruiting arms 24 are typically configured to (a) pull the native atrio-ventricular valve radially inward toward the valve frame, and (b) twist the native atrio-ventricular valve around the valve frame, by recruiting and deflecting at least a portion of the chords of the native atrioventricular valve. Typically, the recruitment and deflection of the chords in this manner serves to prevent obstruction of the left ventricular outflow tract by portions of the native mitral valve apparatus.

For some applications (not shown), the atrial part is coupled directly to the cylindrical part (i.e., not via the protruding struts). For example, the atrial part may be coupled directly to cells and/or to cell junctions of the cylindrical part. For some applications, the atrial part is coupled directly to the cylindrical part using sutures. For some such applications, the sutures act as hinges, such that the atrial part is able to move relative to the cylindrical part. Alternatively, the atrial part is coupled directly to the cylindrical part using a different method, such as welding, gluing, or a different method. Typically, in such cases, the coupling is such that there is axial overlap between the atrial part and the cylindrical part of the valve frame, along the height of the cylindrical part, as described above. That is to say that, typically, the frustoconical portion of the atrial part is coupled to the cylindrical part, such that the frustoconical portion of the atrial part extends from an axial location along the cylindrical part that is in the lowest 90 percent (e.g., the lowest 70 percent, or the lowest 50 percent) of a height of the cylindrical part.

Figure 6A:
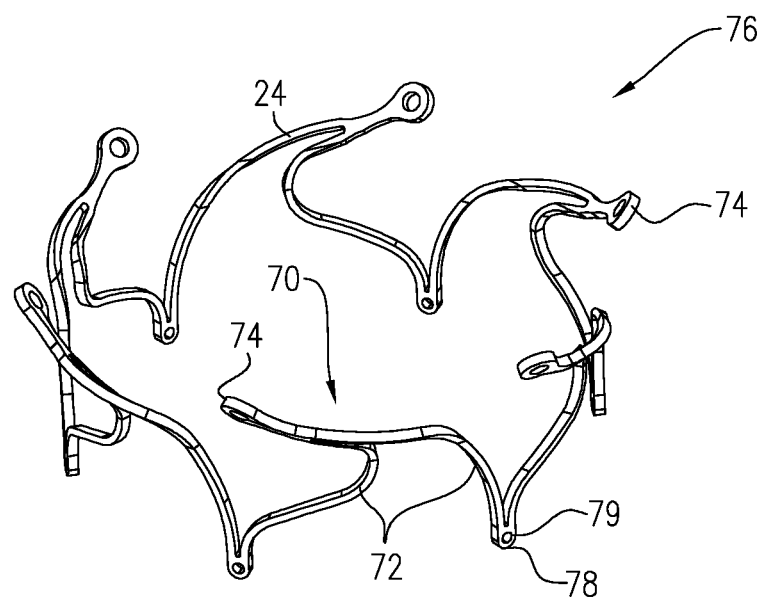
FIG. 6A is a schematic illustration of chord-recruiting arms of a valve frame, in accordance with some applications of the present invention.
Figure 6B:
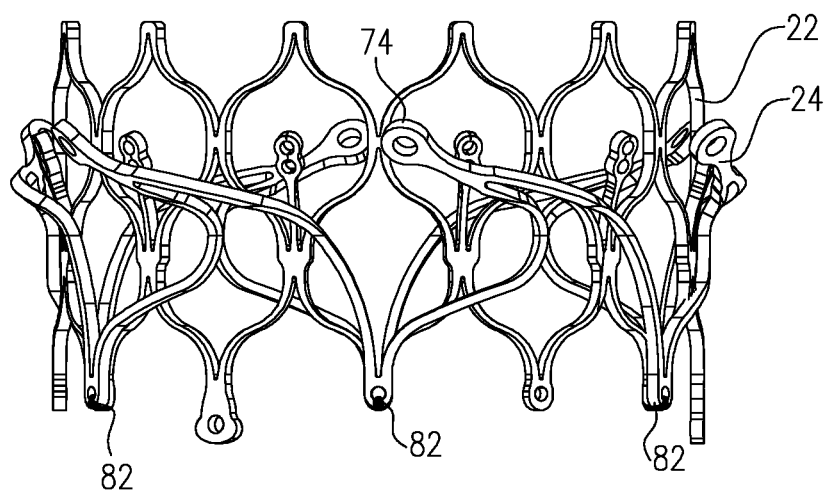
FIG. 6B is a schematic illustration of the chord-recruiting arms of FIG. 6A coupled to a cylindrical part of the valve frame, in accordance with some applications of the present invention.

Reference is now made to FIG. 6A, which is a schematic illustration of chord-recruiting arms 24 of valve frame 20, in accordance with some applications of the present invention. Reference is also made to FIG. 6B, which is a schematic illustration of the chord-recruiting arms coupled to cylindrical part 22 of the valve frame. As described hereinabove, for some applications, a plurality of chord-recruiting arms 24 (e.g., more than two and/or fewer than twelve arms) extend from a portion of valve-frame body 21 that is configured to be placed within the subject's ventricle. For example, four chord-recruiting arms or six chord-recruiting arms may extend from the valve-frame body. For some applications, a single chord-recruiting arm 24 extends from a portion of valve-frame body 21 that is configured to be placed within the subject's ventricle. Typically, the chord-recruiting arms extend from cylindrical part 22 of valve-frame body 21, as shown in FIG. 6B.

For some applications, each of chord-recruiting arms 24 is defined by a pair 70 of struts 72, which extend from respective junctions of the ventricular end of cylindrical part 22. Typically, the struts curve such as to meet each other and form a junction at a tip 74 of the arm. For some applications, all of the chord-recruiting arms are cut from a single piece 76 of a shape memory material (e.g., a shape-memory alloy, such as nitinol and/or copper-aluminum-nickel). The piece of shape-memory material that defines the arms is typically coupled to the cylindrical part of the valve frame, as described in further detail hereinbelow. Typically, the arms are covered in covering material 32 (shown in FIG. 2), e.g., a fabric and/or a polymer (such as expanded polytetrafluoroethylene (ePTFE) and/or polyester).

Typically, chord-recruiting arms 24 of the valve frame are configured to be released from delivery device 40 while valve-frame body 21 of the valve frame is still maintained in an at least partial radially-constrained configuration by the delivery device, as described hereinabove with reference to FIG. 2. In this first configuration of the chord-recruiting arms (referred to herein as the rotation configuration of the chord-recruiting arms), the arms are configured to become deployed among chords of the native atrioventricular valve, and are then configured to (a) pull the native atrio-ventricular valve radially inward toward the valve frame, and (b) twist the native atrio-ventricular valve around the valve frame, by recruiting and deflecting at least a portion of the chords. Subsequently, the valve frame body is allowed to assume its non-radially-constrained configuration, by releasing the valve-frame body from the delivery device. Typically, the assumption of the non-radially-constrained configuration by the valve-frame body causes the configuration of the chord-recruiting arms to change from their first configuration (i.e., their rotation configuration) to a second configuration that is different from the first configuration. In this second configuration, chord-recruiting arms 24 are configured to cause the chords and/or the native valve leaflets to become trapped between the arms and portions of the valve-frame body. Typically, the second configuration of the arms ensures robust anchoring between the trapped chords and/or the native valve leaflets with respect to the valve frame body and the prosthetic valve leaflets.

Typically, a first one of struts 72 of pair 70 of struts that comprise a chord-recruiting arm is longer than a second strut of the pair. The pair of struts is configured such that, when the bases of the struts are held together (when the arms are in their rotation configuration), the arms are relatively long and thin, such that the arms deploy among a relatively large number of chords, and subsequently, recruit and deflect a relatively large number of chords. For some applications, in this configuration, each of the arms has a length of more than 10 mm (e.g. more than 20 mm, or more than 25 mm), measured along the axis of the arm. Typically, the arms are configured such that, when the arms are in the rotation configuration, (a) the arms extend radially from the valve-frame body, (b) the arms extend axially from a ventricular end of the valve-frame body (i.e., the end of the valve frame body that is configured to be placed within the ventricle) toward an atrial end of the valve-frame body (i.e., the end of the valve frame body that is configured to be placed within the atrium), and (c) the arms curve around outside of the cylindrical part in a given direction of circumferential curvature. As described hereinabove, for some applications, in their rotation configuration, the chord-recruiting arms are configured to extend radially from valve frame and to curve circumferentially around the valve frame, but not to extend axially in either the proximal or the distal direction. Rather, for such applications, in their rotation configuration, the arms extend from the valve frame in the radial direction with the arms disposed in a single plane along the axial direction.

In addition, as described hereinabove, for some applications, in the rotation configuration of the chord-recruiting arms, the outer surfaces of each of the arms has a smooth, convex curvature that extends along substantially the full length of the arm, such that during an initial rotation of the valve frame (against the direction of circumferential curvature of the arm) the chords slide over the outer surfaces of the arm without being recruited or caught by the arm, and without being damaged by the arms. For some applications, by virtue of the arms being shaped in this manner, the initial rotation of the valve frame causes a relatively large number of chords to be positioned such as to be recruited by each of the arms in the subsequent rotation step. During the subsequent rotation of the valve frame (in the direction of the circumferential curvature of the arms), the chords are recruited and deflected by the arms. Typically, in the rotation configuration of the chord-recruiting arms, the inner surface of the arm has a concave curvature and the chords are recruited within the space defined by the concave curvature, during the subsequent rotation by the valve frame.

Typically, the arms are configured such that in the second configuration of the arms (i.e., in the non-radially-constrained configuration of the valve frame) the arms become shorter and (at least at the bases of the arms) the arms become wider, due the bases of the struts separating from each other. Typically, the arms define the three above-mentioned curvatures in the second configuration. That is to say that, when the arms assume the second configuration, (a) the arms extend radially from the valve-frame body, (b) the arms extend axially from a ventricular end of the valve-frame body (i.e., the end of the valve frame body that is configured to be placed within the ventricle) toward an atrial end of the valve-frame body (i.e., the end of the valve frame body that is configured to be placed within the atrium), and (c) the arms curve around outside of the cylindrical part in the given direction of circumferential curvature.

Typically, piece 76 of shape-memory material that defines chord-recruiting arms 24 is coupled to the cylindrical part of the valve frame, via stitching. For some applications, one of the struts of each of the arms meets one of the struts of an adjacent arm at a junction 78. For some applications, the shape memory material defines a hole 79 at the junction, through which a suture is inserted, and the suture is used to create a stitch 82 that stitches the shape-memory material to the cylindrical part of the valve-frame body.

As described hereinabove with reference to FIG. 2, typically, chord-recruiting arms 24 of the valve frame are configured to be released from delivery device 40 while valve-frame body 21 of the valve frame is still maintained in an at least partial radially-constrained configuration by the delivery device. For some applications, the arms are stitched to the cylindrical part at an axial location that is released from the delivery device, even at this stage. For some such applications, the stitches act as hinges, such that the arms pivot about the stitches, with respect to the cylindrical part. For some applications, this allows the arms to extend radially to a greater distance than if the stitches did not provide the aforementioned hinge functionality. Alternatively or additionally, the valve frame includes lever elements, which are configured to cause the chord-recruiting arms to extend radially, as described hereinbelow with reference to FIGS. 7A-B.

As indicated in FIGS. 6A and 6B, typically, tips 74 of chord-recruiting arms 24 are rounded. Alternatively or additionally, a thickened layer of covering material 32 (not shown in FIGS. 6A-B) is disposed over tips 74 of the chord-recruiting arms, such that the tips of the arms are cushioned. For example, cushioning 75 is shown at tips 74 of the chord-recruiting arms in FIG. 2B. Typically, the roundness of the tips and/or the cushioning of the tips is such that the tips of the arms are atraumatic. Further typically, this facilitates movement and rotation of the arms among the subject's chords and allows recruitment and deflection of the chords by the arms, without causing damage to the chords or to other surrounding tissue. For some applications, the roundness and/or cushioning of the tips allows the chords to be guided around the tips during the rotation of the valve frame (e.g., the bidirectional rotation of the valve frame described hereinabove). For some applications, using a thickened layer of covering material 32 on the tips of the arms (i.e., providing cushioning 75) facilitates securement of the trapped chords and native leaflets, after the release of the valve-frame body from the delivery device.

For some applications, covering material 32 (shown in FIG. 1D) is configured such as to provide different functionalities to respective regions of the valve frame. For example, areas of the valve frame that typically come into contact with the chords (such as the chord-recruiting arms and the ventricular rim of the cylindrical portion) are typically covered with a low friction fabric (such as, PTFE) in order to provide low friction with respect to the chords and to allow the movement of these portions with respect to the chords without damaging the tissue. Typically, one or both of the inner and outer surfaces of the chord-recruiting arms are covered with a low friction fabric (such as, PTFE) in order to provide low friction with respect to the chords and to allow the movement of these portions with respect to the chords without damaging the tissue. Other areas of the valve frame may be covered with fabric that induces tissue ingrowth (e.g., a porous fabric), in order to cause these areas to become anchored to tissue of the subject. Such areas typically include portions of atrial part 26 and/or cylindrical part 22 that contact the native atrioventricular valve leaflets.

In general, the chord-recruiting arms typically define (a) a radially-constrained configuration when the arms are maintained in crimped configurations inside the delivery device, as well as (b) a rotation configuration, when the arms are released from the delivery device, but the cylindrical part is maintained in an at least partially radially-constrained configuration by the delivery device, and (c) a fully deployed configuration, when the entire valve-frame body, including the cylindrical part and the atrial part, is released from the delivery device. In the rotation configuration, the arms are configured to recruit and deflect the chords. For some applications, in the rotation configuration, the arms are configured to pivot outwardly with respect to the cylindrical part (e.g., by means of stitches 82, lever elements 80), such that the arms encompass a relatively large span and are thereby able to recruit a large number of chords during the rotation of the valve frame. Typically, there is a relatively large gap between the tips of the arms and the valve frame body in this configuration, by virtue of the arms pivoting outwardly with respect to the cylindrical part. Further typically, in the fully deployed configuration (when the entire valve-frame body, including the cylindrical part and the atrial part, is released from the delivery device), the chord-recruiting arms are configured to be disposed such as to define a relatively small gap G (defined hereinbelow with reference to FIG. 8C) between the tips of the arms and the outer surface of the valve-frame body (e.g., the outer surface of the cylindrical part), such that leaflets and or chords of the native atrioventricular valve are trapped between the arms and the valve-frame body (e.g., the outer surface of the cylindrical part). For some applications, in the fully deployed configuration, the chord-recruiting arms are configured to define pockets P of space (shown in FIG. 8B) between themselves and the valve frame body (e.g., the outer surface of the cylindrical part), by virtue of the inner surfaces of the arms having a concave curvature. Typically, chords that are recruited by the arms and/or tissue of the native valve leaflets are held within these pockets of space.

Figure 7A:
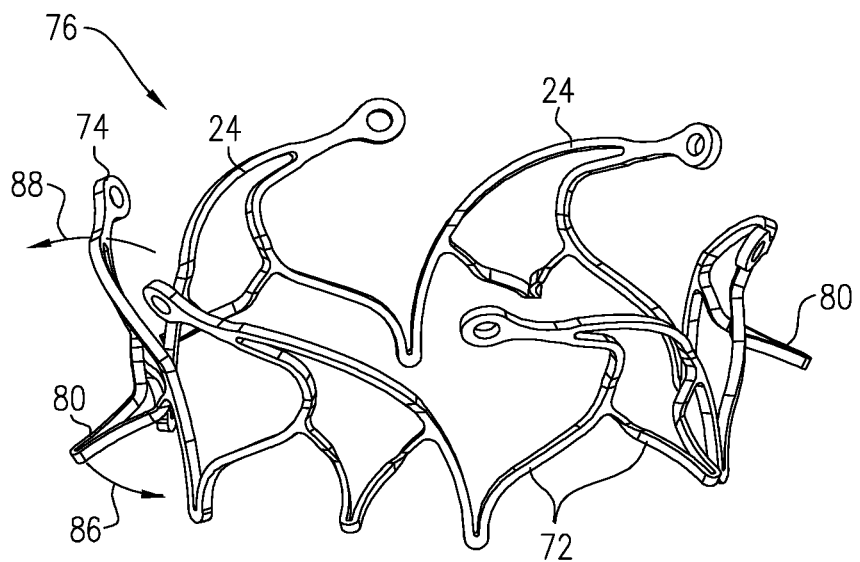
FIGS. 7A and 7B are schematic illustrations of chord-recruiting arms of a valve frame disposed in non-radially-constrained configurations (FIG. 7A), and when lower ends of the arms are held within a delivery device, but the upper ends of the arms have been released from the delivery device (FIG. 7B), in accordance with some applications of the present invention.
Figure 7B:
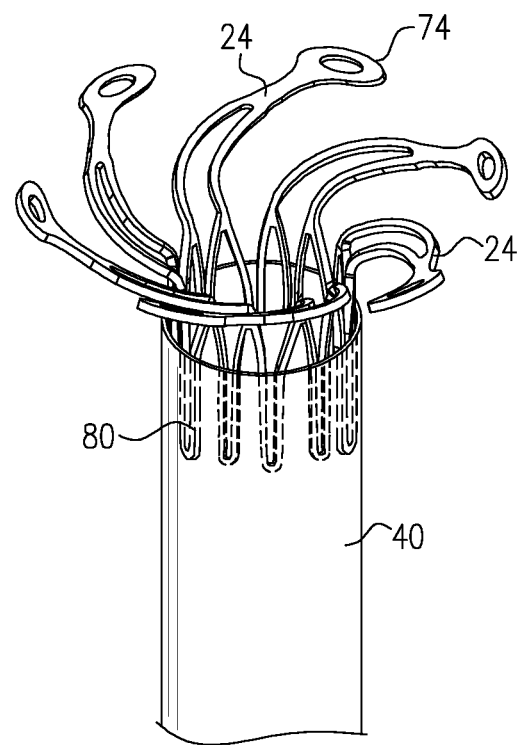

Reference is now made to FIGS. 7A-B, which are schematic illustrations of chord-recruiting arms 24 disposed in non-radially-constrained configurations (FIG. 7A), and when lower ends of the arms are held within delivery device 40, but the upper ends of the arms have been released from the delivery device (FIG. 7B), in accordance with some applications of the present invention. As with many of the other figures, FIGS. 7A-B show chord-recruiting arms 24 in the absence of covering material 32, for illustrative purposes. For some applications, piece 76 of the shape-memory alloy that defines chord-recruiting arms 24, defines lever elements 80. The lever elements are configured to be held within delivery device 40, when the arms are disposed in their rotational configuration (in which the arms are configured to deploy among the chords and then to recruit and deflect the chords). As shown in FIG. 7A, typically, the lever elements are configured to extend from the bases of arms 24 at an angle, when the valve frame is disposed in its non-radially-constrained configuration. By being held within the delivery device, the lever elements are configured to cause the arms to pivot radially outwards, as shown in FIG. 7B. This is indicated by arrows 86 and 88 in FIG. 7A. As shown, by moving (or holding) the lever element in the direction of arrow 86, tip 74 of the arm is configured to pivot radially outwardly in the direction of arrow 88.

Figure 8A:
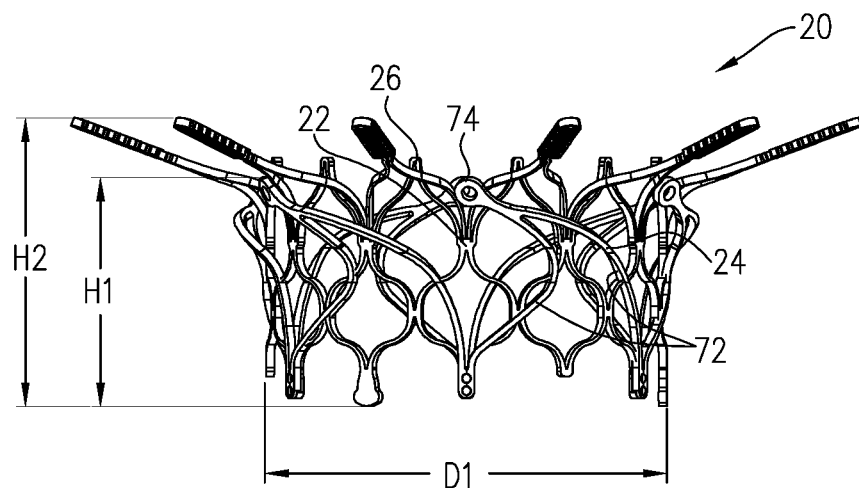
FIGS. 8A, 8B, and 8C are schematic illustrations of respective views of a valve frame in its non-radially-constrained configuration, in accordance with some applications of the present invention.
Figure 8B:
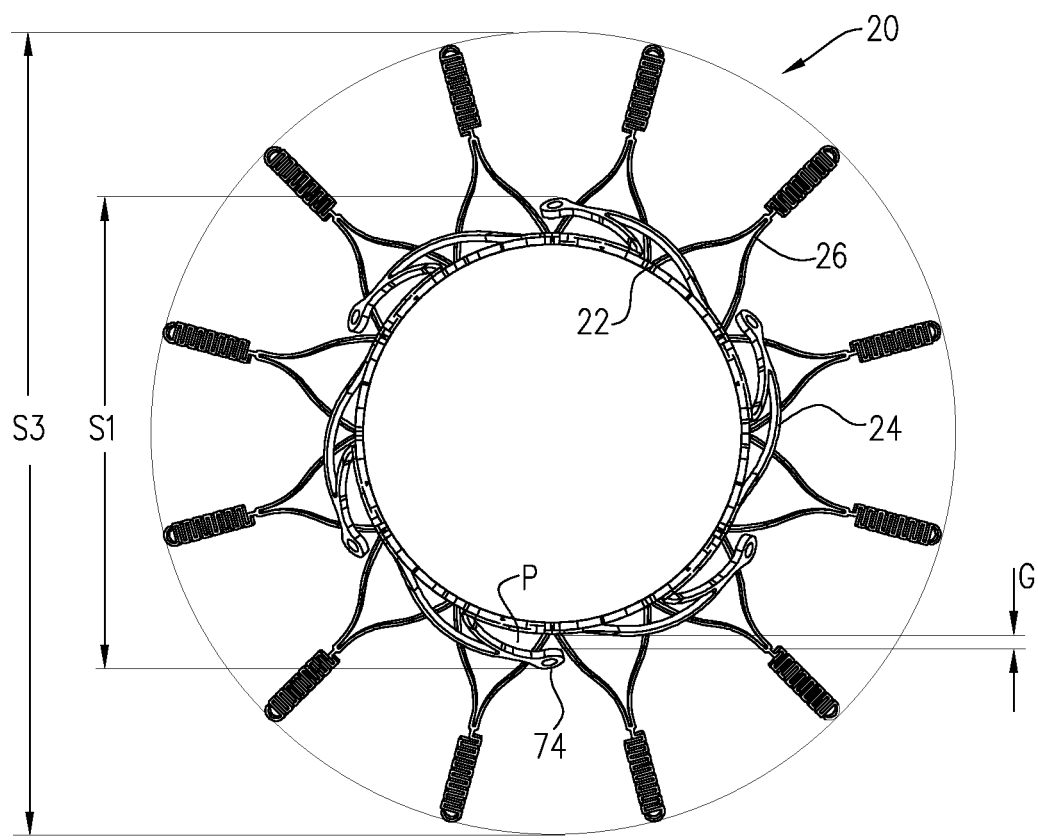
Figure 8C:
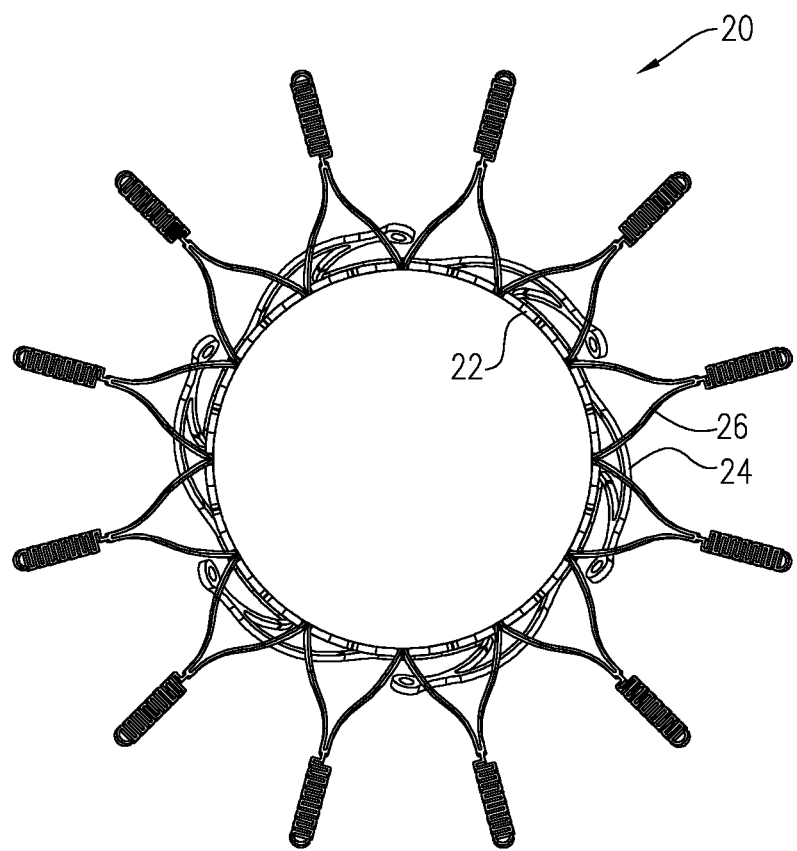
Figure 9A:
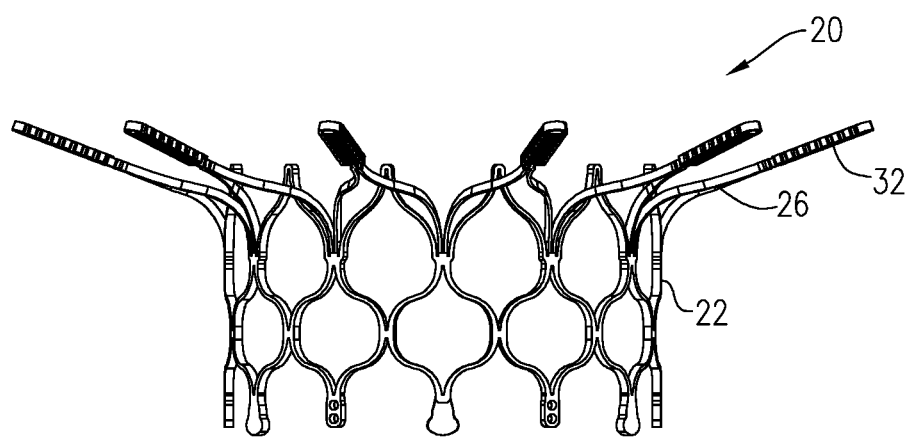
FIGS. 9A and 9B are schematic illustrations of respective views of a valve-frame body of a valve frame, in accordance with some applications of the present invention.
Figure 9B:
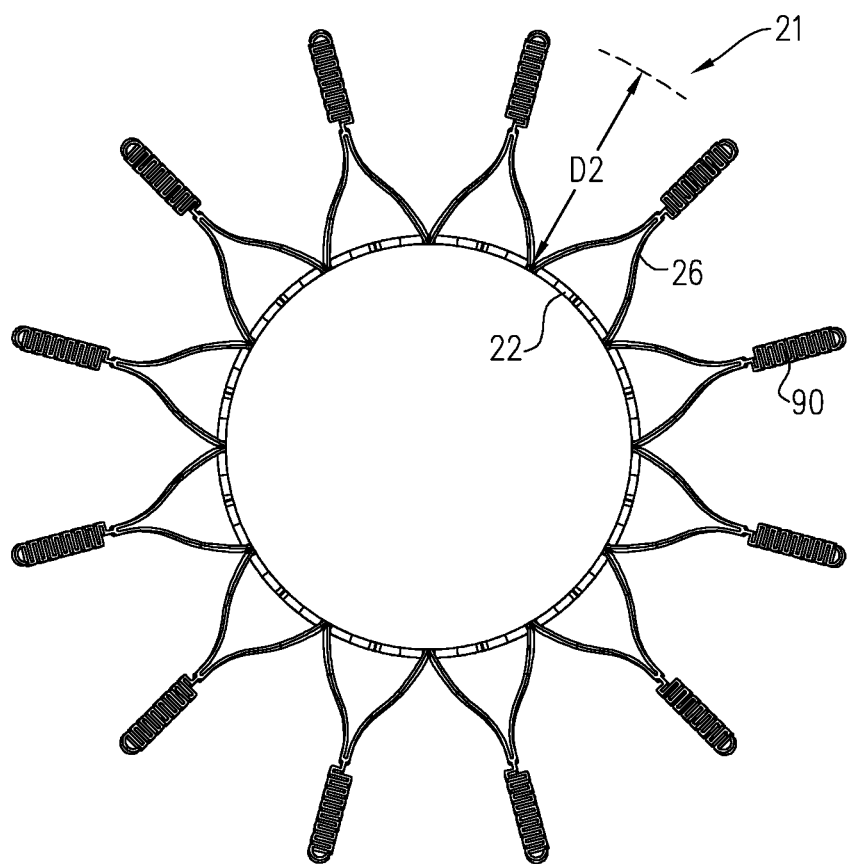

Reference is now made to FIGS. 8A, 8B, and 8C, which are schematic illustrations of respective views of valve frame 20, the figures showing the valve frame in its non-radially-constrained configuration, in accordance with some applications of the present invention. Certain features of valve frame 20 as shown in FIGS. 8A-C (and as the valve frame is also shown in FIGS. 9A-B) differ from the valve frame 20 as described with reference to FIGS. 1A-7B, such features being described hereinbelow. In all other aspects, valve frame 20 as shown in FIGS. 8A-C (and as the valve frame is also shown in FIGS. 9A-B) is generally similar to valve frame 20 as described with reference to FIGS. 1A-7B. Certain dimensions of valve frame 20 are described with respect to valve frame 20 as shown in FIGS. 8A-C and FIGS. 9A-B. Typically, generally similar dimensions are applicable to valve frame 20 as shown in FIGS. 1A-7B, mutatis mutandis.

For some applications, cylindrical part 22 and atrial part 26 of valve frame 20 are made of a single integrally-formed piece of shape memory material, as shown in FIGS. 8A-C.

Referring to FIGS. 8A-C, for some applications, valve frame 20 is configured such that in the absence of any forces acting on the valve frame (e.g., in the non-radially-constrained configuration of the valve frame), a height H1 of each of chord-recruiting arms 24 is more than 5 mm (e.g., more than 7 mm), and/or less than 20 mm (e.g., less than 15 mm), for example, 5-20 mm, or 7-15 mm. For some applications, in this configuration of the valve frame, a total height H2 of the valve frame is greater than 10 mm (e.g., greater than 15 mm), and/or less than 30 mm (e.g., less than 25 mm), e.g., 10-30 mm, or 15-25 mm.

Referring to FIGS. 8A and 8B, for some applications, valve frame 20 is configured such that in the absence of any forces acting on the valve frame (e.g., in the non-radially-constrained configuration of the valve frame), a diameter D1 of cylindrical part 22 of valve-frame body 21 is greater than 20 mm (e.g., greater than 25 mm), and/or less than 40 mm (e.g., less than 35 mm), e.g., 20-40 mm, or 25-35 mm. For some applications, in this configuration of the valve frame, a span S1 defined by the chord-recruiting arms is greater than 22 mm (e.g., greater than 26 mm), and/or less than 45 mm (e.g., less than 40 mm), e.g., 22-45 mm, or 26-40 mm. For some applications, in this configuration of the valve frame, a gap G between the tips 74 of each of chord-recruiting arms 24, and the outer surface of the valve-frame body is greater than 0.1 mm (e.g., greater than 0.5 mm), and/or less than 6 mm (e.g., less than 5 mm), e.g., 0.1-6 mm, or 0.5-5 mm. For some applications, gap G is between the tips of the chord-recruiting arms, and the cylindrical part. Alternatively or additionally, gap G is between the tips of the chord-recruiting arms, and atrial part 26 (e.g., frustoconical portion 30 of atrial part 26). Referring to FIG. 8B, typically, in the non-radially-constrained configuration of the valve frame, the chord-recruiting arms are configured such as to define pockets P of space between themselves and the valve frame body (e.g., the outer surface of the cylindrical part), by virtue of the inner surfaces of the arms having a concave curvature. Typically, chords that are recruited by the arms and/or tissue of the native valve leaflets are held within these pockets of space. For some applications, the valve frame is shape set such that in the non-radially-constrained configuration of the valve frame there is no gap between the tips 74 of each of chord-recruiting arms 24, and the outer surface of the valve-frame body. For some applications, the arms are preloaded such that arms exert a force upon the outer surface of the valve frame body, for example, via shape-setting of the arms (such that, in such applications, if it were not for the frame blocking the tips of the arms, gap G would be less than zero).

Referring again to FIG. 2, for some applications, when chord-recruiting arms 24 of the valve frame have been released from a delivery device 40 while valve-frame body 21 of the valve frame is still maintained in an at least partial radially-constrained configuration by the delivery device (i.e., when the chord-recruiting arms are disposed in their rotation configuration), the chord-recruiting arms 24 are configured to define a span S2 that is greater than 20 mm (e.g., greater than 25 mm), and/or less than 40 mm (e.g., less than 35 mm), e.g., 20-40 mm, or 25-35 mm.

Reference is now made to FIGS. 9A and 9B, which are schematic illustrations of respective views of valve-frame body 21 of valve frame 20, in accordance with some applications of the present invention. For illustrative purposes, FIGS. 9A-B show the valve-frame body in the absence of chord-recruiting arms 24 of the valve frame.

As described hereinabove, typically, valve-frame body 21 is a stent-like structure that comprises struts of the shape-memory material and that is shaped to define a generally-cylindrical shape. For some applications, a plurality of extensions 90 extend radially from the portion of the valve-frame body that is configured to extend into the atrium. Typically, the extensions are configured to prevent migration of the prosthetic valve and/or the valve frame into the subject's ventricle. Alternatively or additionally, the extensions are configured such that when the valve-frame body radially expands, the native valve leaflets become trapped between the extensions and the chord-recruiting arms. For some applications, the extensions are flexible (for example, the extensions may be shaped as springs, as shown), and are configured to conform with the shape of tissue of the mitral annulus on the atrial side of the mitral valve.

For some applications, valve frame 20 is configured such that in the absence of any forces acting on the valve frame (e.g., in the non-radially-constrained configuration of the valve frame), atrial part 26 encompasses a radial distance D2 from the outer surface of cylindrical part 22 that is greater than 5 mm (e.g., greater than 10 mm), and/or less than 25 mm (e.g., less than 20 mm), e.g., 5-25 mm, or 10-20 mm Referring again to FIG. 8B, for some applications, in this configuration of the valve frame, atrial part 26 is configured to define a span S3 that is greater than 30 mm (e.g., greater than 35 mm), and/or less than 80 mm (e.g., less than 70 mm), e.g., 30-80 mm, or 35-70 mm.

Figure 10A:
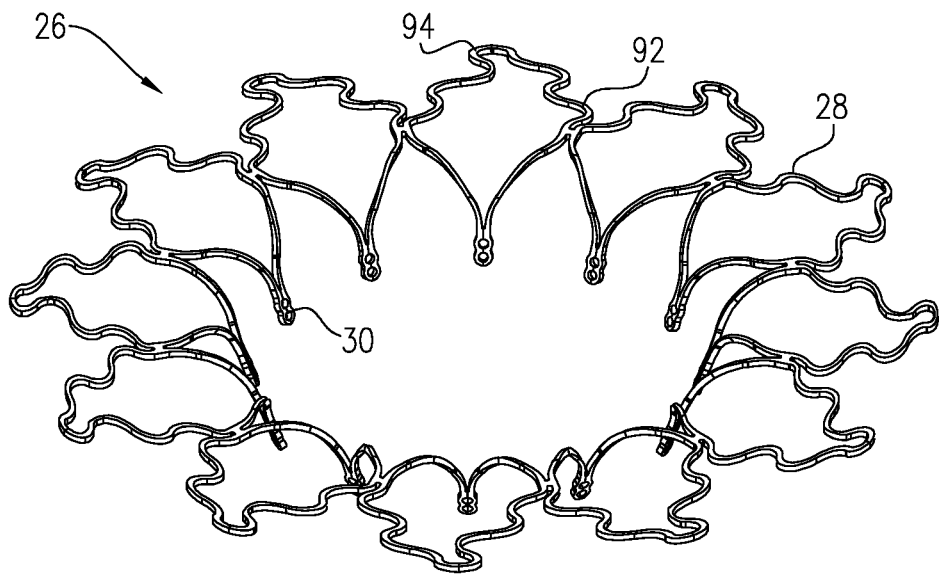
FIGS. 10A and 10B are schematic illustrations of an atrial part of a valve frame, struts of the atrial part having an undulating pattern, in accordance with some applications of the present invention.
Figure 10B:
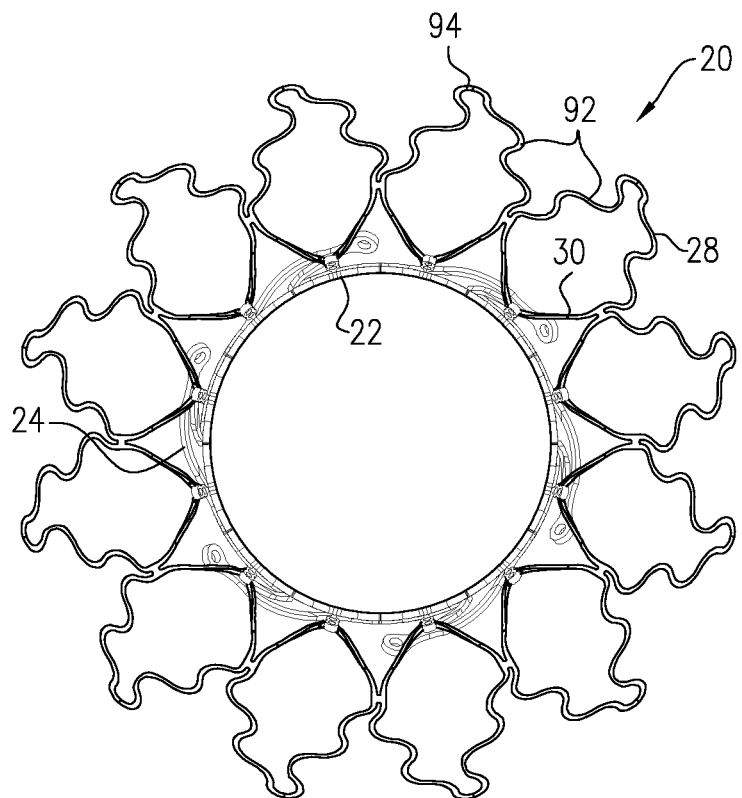

Reference is now made to FIGS. 10A and 10B, which are schematic illustrations of atrial part 26 of valve frame 20, struts 92 of which have an undulating pattern, in accordance with some applications of the present invention. FIG. 10 A shows only the atrial part of the valve frame, while FIG. 10B shows a top view of the atrial part coupled to cylindrical part 22 and chord-recruiting arms 24. For some applications, struts of disc-shaped portion (i.e., flange) 28 of the atrial part have an undulating pattern as shown. Typically, the undulating struts are configured to provide the cells of the flange with flexibility, such that the flange is able to adapt its shape to conform with changes in the shape of tissue of the mitral annulus on the atrial side of the mitral valve that the flange contacts. For some applications, the undulating struts are configured to provide the cells a better distribution of stress and strain when bending, relative to straight struts. For some applications, the cells of the flange have a circumferential curvature, such that outer tips 94 of the cells point in a given circumferential direction. Typically, the circumferential curvature of the cells is in the opposite direction from the direction of circumferential curvature of the chord-recruiting arms. For some applications, by defining this circumferential curvature, the cells of the flange are configured to act as anti-recoil elements, and to prevent rotation of the valve frame in the opposite direction to the direction in which it was rotated.

Reference is now made to FIGS. 11A, 11B, 11C, 11D, 11E, and 11F, which are schematic illustrations of respective steps of the delivery and deployment of a prosthetic mitral valve, via a transseptal approach, in accordance with some applications of the present invention. Typically, the prosthetic mitral valve includes valve frame body as described hereinabove, with prosthetic valve leaflets 23 sutured to the cylindrical part, and/or otherwise coupled to cylindrical part 22 of the valve frame, e.g., as shown in FIG. 1D. As described hereinabove, in accordance with respective applications, the prosthetic mitral valve is delivered transseptally (i.e., via the vena cava, the right atrium, and the interatrial septum), transapically (i.e., via the apex of the left ventricle), and/or via a different delivery path. FIGS. 11A-F shows steps of delivery and deployment of a prosthetic mitral valve, via the transseptal approach, by way of illustration and not limitation.

Figure 11A:
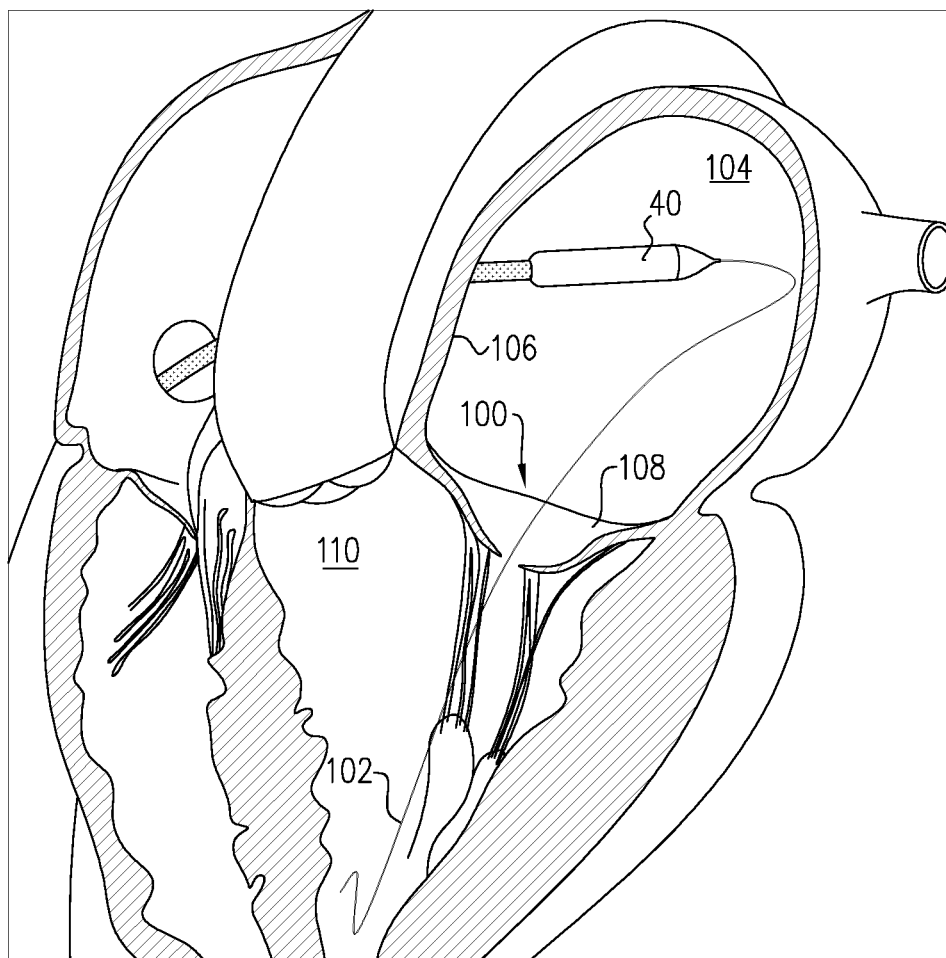
FIGS. 11A, 11B, 11C, 11D, 11E, and 11F are schematic illustrations of respective steps of the deployment of a prosthetic mitral valve via a transseptal approach, in accordance with some applications of the present invention.
Figure 11B:
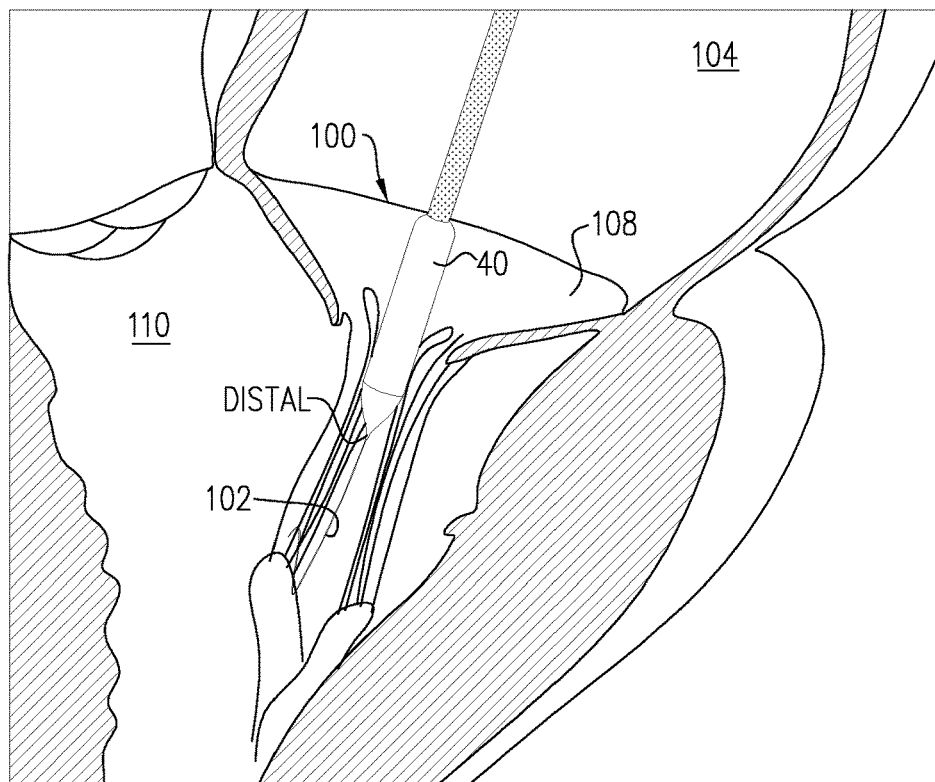
Figure 11C:
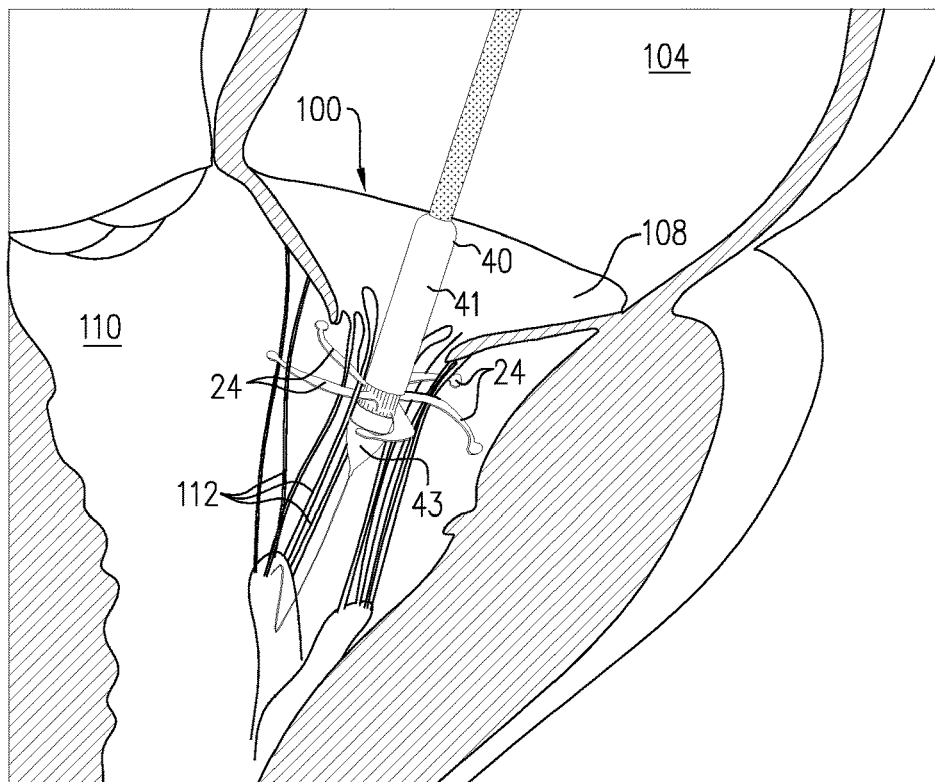

Typically, delivery device 40 (e.g., delivery catheter) is guided toward the subject's native mitral valve 100 over a guidewire 102. As shown in FIG. 11A, the distal end of delivery device 40 is typically advanced into the subject's left atrium 104, via the interatrial septum 106. The distal end of the delivery device is advanced toward the native mitral valve, and is advanced through leaflets 108 of the native mitral valve and into left ventricle 110, as shown in FIG. 11B. When the distal end of the delivery device is disposed within the left ventricle, chord-recruiting arms 24 are allowed to at least partially radially expand, and assume their rotation configurations, as shown in FIG. 11C. For some applications, the arms are allowed to assume non-radially-constrained configurations by releasing the arms from being radially constrained by the delivery device, e.g., by partially retracting proximal overtube 41, and/or by partially advancing distal nosecone 43. Typically, the chord-recruiting arms are shape set to extend radially from valve-frame body 21 and to curve circumferentially around the valve-frame body (e.g., in the clockwise direction, as shown), upon assuming their rotation configurations. For some applications, the chord-recruiting arms are further configured to extend axially toward the subject's atrium. Typically, the chord-recruiting arms are configured to become deployed among chords 112 of the native mitral valve upon being released from the delivery device.

Figure 11D:
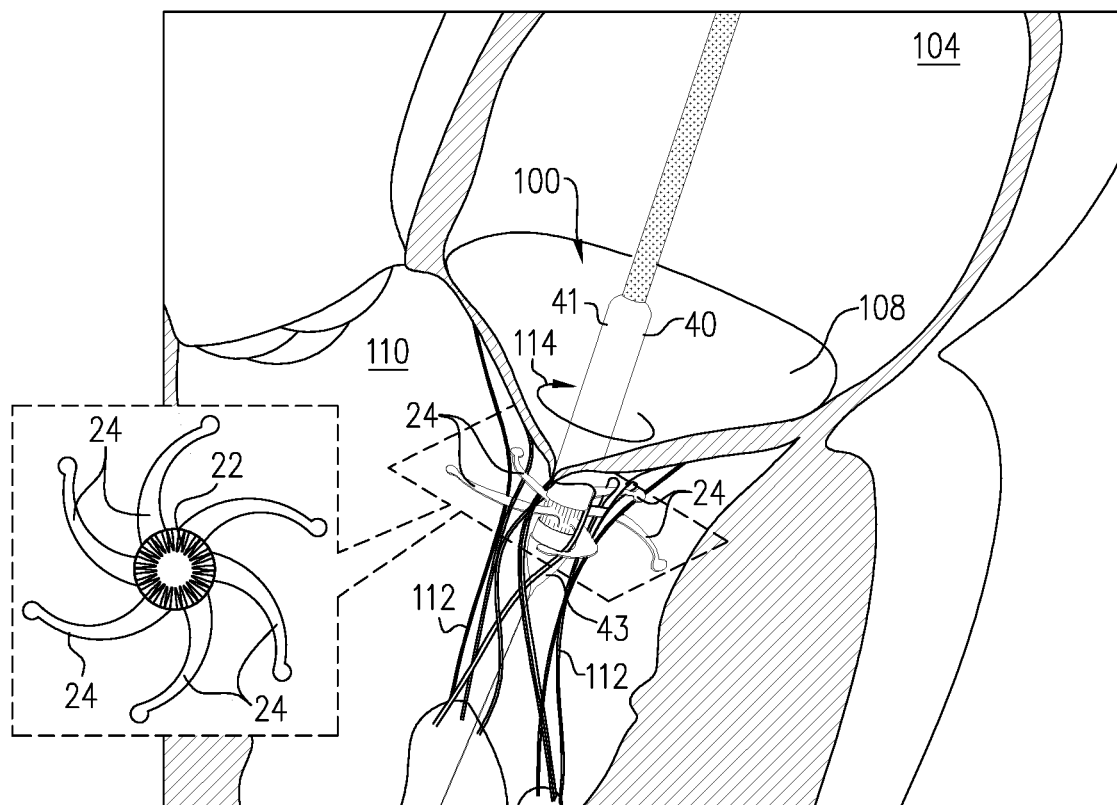

As shown in FIG. 11D, subsequent to the chord-recruiting arms 24 being deployed among chords of the native mitral valve, at least a portion of valve frame 20 is rotated in the direction of arrow 114, such as to cause chord-recruiting arms 24 to (a) pull the native atrioventricular valve radially inward toward the valve frame, and (b) twist the native atrioventricular valve around the valve frame, by recruiting and deflecting at least a portion of the chords. Typically, the chord-recruiting arms 24 are configured to curve in a given circumferential direction with respect to the longitudinal axis of the valve frame. For example, the arms may curve in a clockwise direction or in a counter-clockwise direction with respect to the longitudinal axis of the valve frame. Typically, subsequent to chord-recruiting arms 24 being deployed among chords of the native mitral valve, the valve frame is rotated in the same circumferential direction as the direction of the circumferential curvature of the arms. In the example shown in FIG. 11D, the arms curve in the clockwise circumferential direction (as viewed from left atrium 104), and the valve frame is rotated in this direction.

As described hereinabove, for some applications, prior to rotating the valve frame in the same circumferential direction as the direction of the circumferential curvature of the arms, the valve frame is rotated in the opposite circumferential direction. For some applications, the delivery device 40 is configured such as to automatically perform the initial rotation of the valve frame through a given angle against the direction of circumferential curvature of the arm, and to subsequently rotate the valve frame though a predetermined angle in the direction of the circumferential curvature of the arms. For some applications, in the rotation configuration of the arms (shown in FIGS. 11C-D), the outer surfaces of each of the arms has a smooth, convex curvature that extends along substantially the full length of the arm, such that during the initial rotation (against the direction of circumferential curvature of the arm) the chords slide over the outer surfaces of the arm without be recruited or caught by the arm. For some applications, by virtue of the arms being shaped in this manner, the initial rotation of the valve frame causes a relatively large number of chords to be positioned such as to be recruited by each of the arms in the subsequent rotation step. During the subsequent rotation of the valve frame (in the direction of the circumferential curvature of the arms, e.g., the direction of arrow 114 as shown in FIG. 11D), the chords are recruited and deflected by the arms. Typically, in the rotation configuration of the arms (shown in FIGS. 11C-D), the inner surface of the arm has a concave curvature and the chords are recruited within the space defined by the concave curvature, during the subsequent rotation by the valve frame.

Figure 11E:
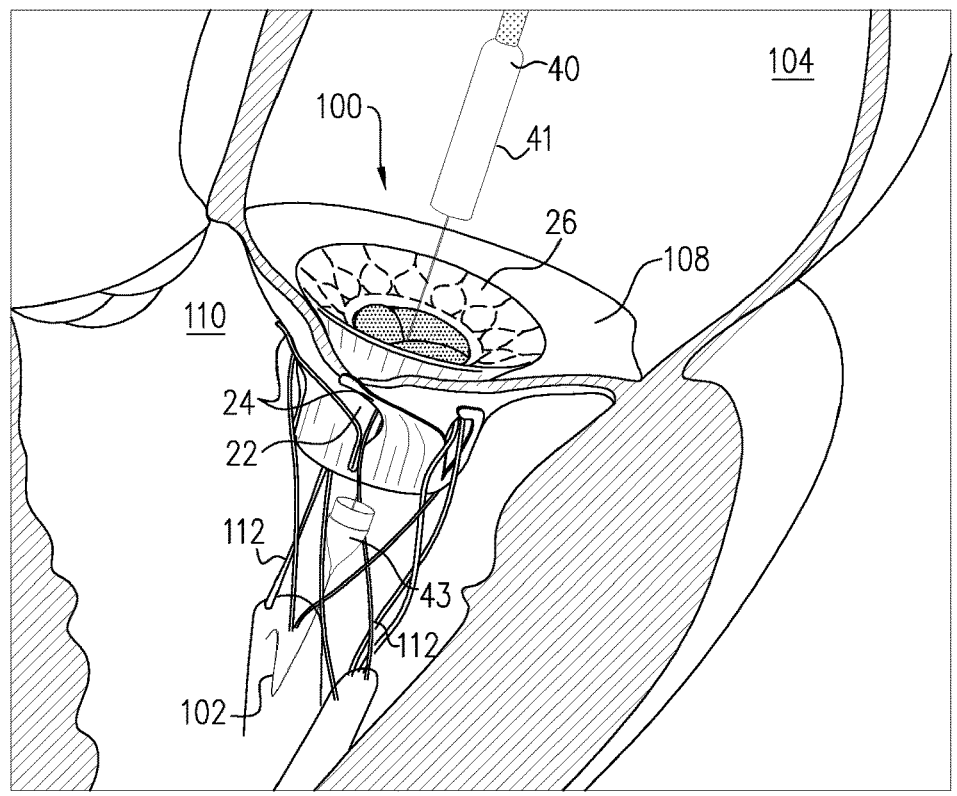
Figure 11F:
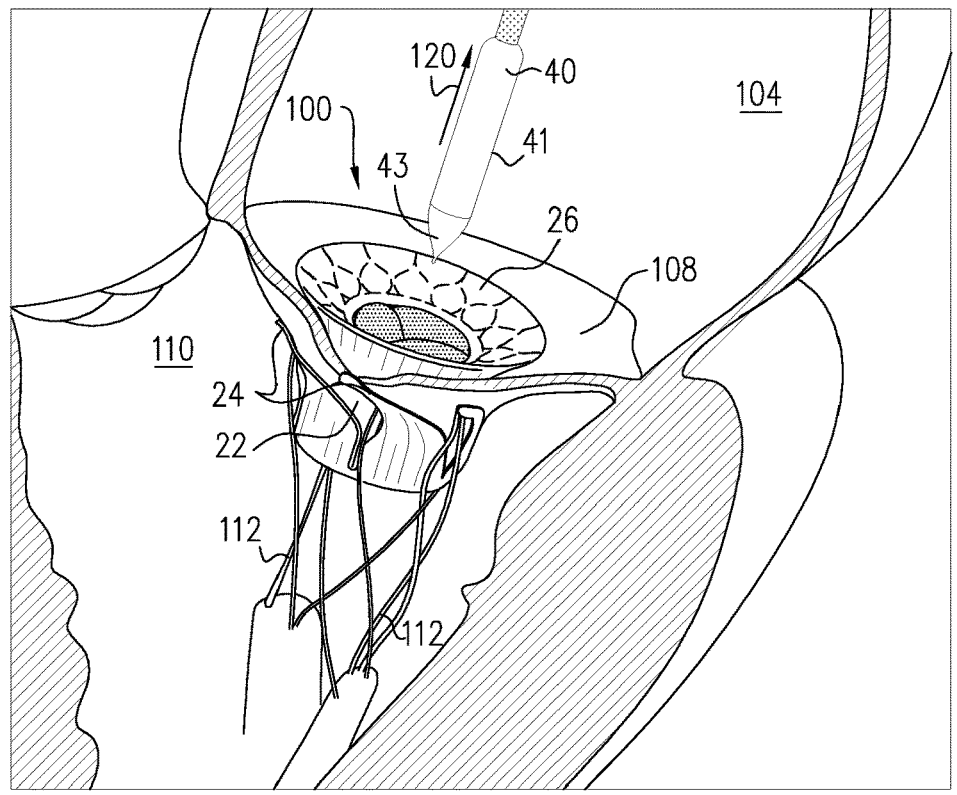

Subsequent to chord-recruiting arms 24 having been released and valve frame 20 having been rotated, valve-frame body 21 (i.e., cylindrical part 22 and atrial part 26 of the valve frame) is allowed to assume its non-radially-constrained configurations. For some applications, the atrial part is allowed to assume its non-radially-constrained configuration by releasing the atrial part from the delivery device, e.g., by retracting proximal overtube 41. For some applications, the cylindrical part is allowed to assume its non-radially-constrained configuration by releasing the cylindrical part from the delivery device, e.g., by advancing distal nosecone 43. FIG. 11E shows both cylindrical part 22 and atrial part 26 in their non-radially-constrained (i.e., radially-expanded) configurations. Typically, by the valve-frame body assuming its non-radially-constrained configuration, the valve-frame body is configured to trap the native valve leaflets 108 in a partially closed and twisted configuration, to thereby at least partially seal a space between the native mitral valve and the prosthetic valve. For example, the cylindrical part may be configured to radially expand such as to trap the native valve leaflets between the cylindrical part and the chord-recruiting arms, and/or the atrial part may be configured to radially expand such as to trap the native valve leaflets between the atrial portion and the chord-recruiting arms. For some applications, the trapping of native valve leaflets 108 in a partially closed and twisted configuration is achieved by trapping the chords (which are attached to the leaflets) in twisted configurations. Subsequent to the above described steps being performed, delivery device 40 is typically then retracted in its entirety from the subject's left atrium, as indicated by arrow 120 in FIG. 11F.

The apparatus and methods described herein are typically performed with respect to a subject's mitral valve and/or with respect to a subject's tricuspid valve. Although some embodiments of the apparatus and methods have been described primarily in relation to a mitral valve, the scope of the present invention includes applying any of the apparatus and methods described hereinabove to the tricuspid valve, mutatis mutandis.

For some applications, apparatus and methods described herein are performed in conjunction with apparatus and methods described in US 2015/0173897 to Raanani, which is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus comprising:
   a valve frame configured to support the prosthetic valve within the native atrio-ventricular valve, the valve frame comprising:
      a valve-frame body, comprising:
         an atrial part comprising a disc-shaped portion configured to be deployed on an atrial side of the valve annulus; and
         a cylindrical part configured to couple to the prosthetic valve leaflets and configured to be deployed such that a ventricular end of the cylindrical part is disposed within the ventricle; and
      a plurality of chord-recruiting arms configured to:
         while the cylindrical part is at least partly radially constrained, assume a rotation configuration in which the chord-recruiting arms extend at least radially from the ventricular end of the cylindrical part and curve circumferentially around the cylindrical part in a given circumferential direction, wherein, in the rotation configuration of the chord-recruiting arms, the chord-recruiting arms are configured to recruit the chords when
         at least a portion of the valve frame is rotated in the given circumferential direction, and while the cylindrical part is not radially constrained, assume a fully-deployed configuration in which the chord-recruiting arms extend less radially and more axially toward the atrial part, relative to the rotation configuration, such that the recruited chords and/or tissue of the native atrio-ventricular valve are trapped between the chord-recruiting arms and the valve-frame body.

2. The apparatus according to claim 1, wherein an outer surface of each of the chord-recruiting arms is covered with a low-friction fabric, such as to allow movement of the outer surface with respect to the chords without damaging tissue.

3. The apparatus according to claim 1, wherein an inner surface of each of the chord-recruiting arms is covered with a low-friction fabric, such as to allow movement of the inner surface with respect to the chords without damaging tissue.

4. The apparatus according to claim 1, wherein a tip of each of the chord-recruiting arms is rounded such as to guide the chords around the tip of the chord-recruiting arm without damaging tissue.

5. The apparatus according to claim 1, wherein a tip of each of the chord-recruiting arms is cushioned such as to guide the chords around the tip of the chord-recruiting arm without damaging tissue.

6. The apparatus according to claim 1, further comprising a delivery device configured to:
- deliver the valve frame to the native atrio-ventricular valve,
- subsequently, deploy the plurality of chord-recruiting arms among the chords of the native atrio-ventricular valve, while maintaining the cylindrical part in an at least partially radially constrained configuration, such that the chord-recruiting arms assume the rotation configuration, and
- while the chord-recruiting arms are disposed in the rotation configuration:
  - initially rotate at least the portion of the valve frame in an opposite circumferential direction from the direction of circumferential curvature of the chord-recruiting arms; and
  - subsequently, rotate at least the portion of the valve frame in the direction of circumferential curvature of the chord-recruiting arms, such as to cause the plurality of chord-recruiting arms to (a) pull the native atrio-ventricular valve radially inward toward the valve-frame body, and (b) twist the native atrio-ventricular valve around the valve-frame body, by recruiting and deflecting the chords.

7. The apparatus according to claim 6, wherein, subsequently to rotating at least the portion of the valve frame, the delivery device is configured to release the atrial part and the cylindrical part of the valve frame, to thereby cause the native atrio-ventricular valve to be held (a) radially inwardly toward the valve-frame body and (b) twisted around the valve-frame body, by causing the tissue of the native atrio-ventricular valve to become trapped between the chord-recruiting arms and the valve-frame body.

8. The apparatus according to claim 1, wherein, in the fully-deployed configuration, the chord-recruiting arms are configured to define pockets of space between themselves and the valve-frame body by virtue of a curvature of the chord-recruiting arms, such that the recruited chords and/or the tissue of the native atrio-ventricular valve are trapped in the pockets.

9. The apparatus according to claim 1, wherein, in the rotation configuration, each of the chord-recruiting arms has a length of more than 10 mm, yet, in the fully-deployed configuration, a gap between a tip of each of the chord-recruiting arms and the valve-frame body is less than 6 mm.

10. The apparatus according to claim 1,
- wherein each of the chord-recruiting arms comprises a pair of struts, which have respective bases at the ventricular end of the cylindrical part and curve so as to meet each other at a tip of the chord-recruiting arm, and
- wherein, in the fully-deployed configuration, each of the chord-recruiting arms is shorter, relative to the rotation configuration, due to the bases of the pair of struts being farther from one another.

11. A method for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the method comprising:
- delivering a valve frame to the native atrio-ventricular valve, the valve frame including:
  - a valve-frame body, including:
    - an atrial part comprising a disc-shaped portion configured to be deployed on an atrial side of the valve annulus; and
    - a cylindrical part to which the prosthetic valve leaflets are coupled, the cylindrical part configured to be deployed such that a ventricular end of the cylindrical part is disposed within the ventricle; and
  - a plurality of chord-recruiting arms configured to extend at least radially from the ventricular end of the cylindrical part;
- deploying the chord-recruiting arms among the chords of the native atrio-ventricular valve, while the cylindrical part is maintained in an at least partially radially constrained configuration, such that the chord-recruiting arms assume a rotation configuration in which the chord-recruiting arms extend at least radially from the ventricular end of the cylindrical part, and curve circumferentially around the cylindrical part in a given circumferential direction;
- subsequently, rotating at least a portion of the valve frame in the direction of circumferential curvature of the chord-recruiting arms, such that the chord-recruiting arms recruit the chords; and
- subsequently, releasing the atrial part and cylindrical part of the valve frame, thereby causing the chord-recruiting arms to assume a fully-deployed configuration in which the chord-recruiting arms extend less radially and more axially toward the atrial part, relative to the rotation configuration, such that the recruited chords and/or tissue of the native atrio-ventricular valve are trapped between the chord-recruiting arms and the valve-frame body.

12. The method according to claim 11, wherein an outer surface of each of the chord-recruiting arms is covered with a low-friction fabric, such as to allow movement of the outer surface with respect to the chords without damaging tissue.

13. The method according to claim 11, wherein an inner surface of each of the chord-recruiting arms is covered with a low-friction fabric, such as to allow movement of the inner surface with respect to the chords without damaging tissue.

14. The method according to claim 11, wherein a tip of each of the chord-recruiting arms is rounded such as to guide the chords around the tip of the chord-recruiting arm without damaging tissue.

15. The method according to claim 11, wherein a tip of each of the chord-recruiting arms is cushioned such as to guide the chords around the tip of the chord-recruiting arm without damaging tissue.

16. The method according to claim 11, wherein rotating at least the portion of the valve frame in the direction of circumferential curvature of the chord-recruiting arms comprises causing the plurality of chord-recruiting arms to (a) pull the native atrio-ventricular valve radially inward toward the valve-frame body, and (b) twist the native atrio-ventricular valve around the valve-frame body, by recruiting and deflecting the chords.

17. The method according to claim 16, wherein releasing the atrial part and the cylindrical part of the valve frame causes the native atrio-ventricular valve to be held (a) radially inwardly toward the valve-frame body and (b) twisted around the valve-frame body, by causing the tissue of the native atrio-ventricular valve to become trapped between the chord-recruiting arms and the valve-frame body.

18. The method according to claim 11, wherein releasing the atrial part and the cylindrical part of the valve frame comprises causing the chord-recruiting arms to define pockets of space between themselves and the valve-frame body by virtue of a curvature of the chord-recruiting arms, such that the recruited chords and/or the tissue of the native atrio-ventricular valve are trapped in the pockets.

19. The method according to claim 11, further comprising rotating at least the portion of the valve frame in an opposite circumferential direction from the direction of circumferential curvature of the chord-recruiting arms before attempting to recruit the chords by rotating the portion of the valve frame in the direction of circumferential curvature of the chord-recruiting arms.

20. The method according to claim 11, wherein, in the rotation configuration, each of the chord-recruiting arms has a length of more than 10 mm, yet, in the fully-deployed configuration, a gap between a tip of each of the chord-recruiting arms and the valve-frame body is less than 6 mm.

21. The method according to claim 11,
wherein each of the chord-recruiting arms comprises a pair of struts, which have respective bases at the ventricular end of the cylindrical part and curve so as to meet each other at a tip of the chord-recruiting arm, and
wherein, in the fully-deployed configuration, each of the chord-recruiting arms is shorter, relative to the rotation configuration, due to the bases of the pair of struts being farther from one another.

22. Apparatus for use with prosthetic valve leaflets that are configured to be deployed within a native atrio-ventricular valve that is disposed between an atrium and a ventricle of a heart of a mammalian subject, the native atrio-ventricular valve including a valve annulus, valve leaflets, chords, and papillary muscles, the apparatus comprising:
a valve frame configured to support the prosthetic valve within the native atrio-ventricular valve, the valve frame comprising:
an atrial part comprising a flange configured to be deployed on an atrial side of the valve annulus, and a frustoconical portion; and
a cylindrical part configured to couple to the prosthetic valve leaflets and configured to be deployed such that a ventricular end of the cylindrical part is disposed within the ventricle,
wherein the flange comprises cells comprising wavy borders configured to provide the cells of the flange with flexibility, such that the flange is able to adapt its shape to conform with changes in a shape of tissue on the atrial side of the valve annulus,
wherein the cells are curved circumferentially, such that outer tips of the cells point in a given circumferential direction, and
wherein the valve frame further comprises chord-recruiting arms that are configured to curve around the cylindrical part circumferentially in an opposite direction of circumferential curvature from the given circumferential direction.

23. The apparatus according to claim 22, wherein the frustoconical portion is coupled to an outside of the cylindrical part.

24. The apparatus according to claim 22, wherein the cells comprise the wavy borders at least along respective sides of the cells.

25. The apparatus according to claim 22, wherein each of the wavy borders undergoes at least five reversals in a direction of curvature.

* * * * *